United States Patent [19]
Komly et al.

[11] Patent Number: 5,955,260
[45] Date of Patent: Sep. 21, 1999

[54] POLYPEPTIDES AND ANTIBODIES CHARACTERISTICS OF PAPILLOMAVIRUS, AND DIAGNOSTIC PROCEDURES AND VACCINES MAKING USE OF THEM

[75] Inventors: Carol Ann Komly; Odile Croissant; Francoise Breitburd, all of Paris, France

[73] Assignee: Institut Pasteur and Institut National de la Sante et de la Recherche Medicale, France

[21] Appl. No.: 08/426,648

[22] Filed: Apr. 21, 1995

Related U.S. Application Data

[62] Continuation of application No. 08/232,588, Apr. 25, 1994, abandoned, which is a continuation of application No. 07/999,583, Dec. 30, 1992, abandoned, which is a continuation of application No. 07/693,088, Apr. 30, 1991, abandoned, which is a continuation of application No. 07/507,007, Apr. 10, 1990, abandoned, which is a continuation of application No. 07/289,452, Dec. 22, 1988, abandoned, which is a continuation of application No. 07/050,904, filed as application No. PCT/FR86/00288, Aug. 22, 1986, abandoned.

[30] Foreign Application Priority Data

Aug. 26, 1985 [FR] France .................................. 85 12750

[51] Int. Cl.⁶ .......................... C12Q 1/70; G01N 33/569; C07K 16/08
[52] U.S. Cl. ............................... 435/5; 436/503; 436/811; 530/387.1
[58] Field of Search .......................... 435/5, 235.1, 948; 436/501, 547, 548, 811, 503; 530/387.1, 806, 826

[56] References Cited

U.S. PATENT DOCUMENTS 4,514,508  4/1985  Hirschfeld ................................... 435/7
4,551,270  11/1985  Danos et al. .............................. 536/27

FOREIGN PATENT DOCUMENTS 0092456  10/1983  European Pat. Off. .
0133123  2/1985  European Pat. Off. .
0192001  8/1986  European Pat. Off. .

OTHER PUBLICATIONS

Waldmann, T.A., Monoclonal Antibodies in Diagnosis and Therapy, Science 252:1657–1662, 1991.
Kremsdorf et al, Journal of Virology:52(3), pp. 1013–1018, Dec. 1984.
Chemical Abstract No. 18873W 102:190 (1985) Kremsdorf et al.
Chemical Abstract No. 126474E 101:366 (1984).
Chemical Abstract No. 121331V, 97:161 (1982).
Heilman et al. Journal of Virology 36:395–407.
Beaudenon, et al. (1986) Nature 321:246–249.
Roseto et al. Journal of Gen Virology (1984) 65:1319–1324.
Georges et al. (1984) Journal of Virology 51:530–538.
Croissant et al. in Clinics and Dermatology, Jablonska et al. vol. 3 Oct.–Dec. 1985, pp. 43–55.
Clad et al. (1982) Virology 118:154–159.
de Villiers et al. (1981) Journal of Virology 40:932–935.
Chemical Abstracts No. 134848A 90:250 (1979).
Chemical Abstract No. 116349r, 94:236 (1981).
Chemical Abstract No. 117603f, 94:357 (1981).

*Primary Examiner*—Donna C. Wortman
*Attorney, Agent, or Firm*—Burns, Doane, Swecker & Mathis, L.L.P.

[57] ABSTRACT

The invention relates to the DNAs of papillomaviruses, and more particularly to the probes derived from these papillomaviruses, as well as procedures for their implementation in the in vitro diagnosis of papillomavirus infections.

6 Claims, 11 Drawing Sheets

FIG. 9

- BgI II (0)
- Hind III (3.8)
- Pst I (8.6)
- Kpn I (12.5)
- Pvu II (22.5)
- Pst I (23.8)
- Pst I (25.7)
- Hind II (26.7)
- Hind III (29.8)
- Xba I (30.2)
- Kpn I (40.4)
- Bgl I (47.6)
- Pst I (51.4)
- Pvu II (73.5)
- Hind II (74.3)
- Ava I - Sma I (76.9)
- Hind II - Npa I (85.7)
- Hind II - Npa I (89.5)
- Xba I (96.2)
- Bgl II (100)

HPV IP2

FIG. 10

0
- Eco RI
- Pst I
- Bgl I

10

20
- Pst I
- Kpn I
- Pst I

30
- Kpn I

40

- Pvu I

50
- Hinc II
- Pst I
- Hinc II
- Hpa I

60

70
- Kpn I
- Bam HI
- Pst I
- Ava I
80
- Hinc II
- Sac I
- Pst I
- Hind III
90
- Pvu II
- Hinc II 100
- Bam HI

HPV IP4

POLYPEPTIDES AND ANTIBODIES CHARACTERISTICS OF PAPILLOMAVIRUS, AND DIAGNOSTIC PROCEDURES AND VACCINES MAKING USE OF THEM

This application is a continuation of application Ser. No. 08/232,388, filed Apr. 25, 1994, abandoned, which is a continuation of application Ser. No. 07/999,583, filed Dec. 30, 1992, abandoned, which is a continuation of application Ser. No. 07/693,088, filed Apr. 30, 1991, abandoned, which is a continuation of application Ser. No. 07/507,007, filed Apr. 10, 1990, abandoned, which is a continuation of application Ser. No. 07/289,452, filed Dec. 22, 1988, abandoned, which is a continuation of application Ser. No. 07/050,904, filed Apr. 22, 1987, abandoned, which was the National Stage of International Application No. PCT/FR86/00288.

The invention relates to the DNAs of papillomaviruses, and more particularly to the probes derived from these papillomaviruses, as well as procedures for their implementation in the in vitro diagnosis of papillomavirus infections.

The expression "papillomavirus" covers a large number of viruses, which have in common the property of being held responsible for several forms of viral infection extending from relatively benign epidermal and mucosal warts to hyperplasias liable to degenerate into intra-epithelial neoplasias and cutaneous cancers. Among these papilloma infections, mention will also be made more especially of epidermodysplasia verruciformis, which will sometimes be designated below by the expression "EV".

A number of types of papillomavirus have already been described. Within the framework of the present patent application many new types and subtypes of papillomavirus will be described which have been isolated from warts or disseminated macular lesions, liable to give rise to the development of skin cancer in a high proportion of those patients affected.

Recent studies have revealed the importance of immune factors and the major role played by various types of virus of human papillomas (HPV) factors which compound the role, already described in the literature, played by various genetic factors and actinic radiation in the pathogenesis of infections of papillomaviruses.

The invention results from observations made during the course of comparative studies of the behaviour of a large number of recently isolated papillomaviruses, the essential genomic characteristic of which will be defined below.

The study of a small number of cases of EV had already led to the characterization of six types of HPV after molecular cloning of their genomes (KREMSDORF. et al, 1982, J. Virol. 43: 436–447 and KREMSDORF et al, 1983, J. Virol. 48: 340–351). These HPV have been divided into three groups as a consequence of the absence of cross-hybridization or very weak cross-hybridization between the genomes of the different groups. The first group includes the HPV3a and 10 which are associated with plane warts observed in some patients suffering from EV and in the population generally: DNA sequences similar to those of HPV3a have been found in a cancer of a patient suffering from EV. The second group comprises HPV5, 8 and 12, the genomes of HPV5 and 8 having been detected in cancers of patients suffering from EV. The third group is constituted at the moment by a single virus, HPV9. With the exception of a recipient of a renal allograft presenting immunosuppression and who was shown to be infected with HPV5, the viruses of the last two groups had only been detected in patients suffering from EV, most of them being infected with several viruses. It is to be noted that, of the 14 types of HPV presently mentioned in the literature (literature references 1–5, 8, 9, 13, 14, 16, 18–20 listed at the end hereof), four were shown to be specifically associated with EV, which is a rare disease.

The experiments which have led to the invention and which have made it possible to isolate a large number of new types and subtypes of papillomaviruses offer the promise of more refined, in vitro diagnostic procedures. More particularly, the invention provides advanced procedures for the identification of papillomaviruses isolated, for example, from lesions or biopsy sections and makes it possible to carry out more precise diagnoses which are likely to result in improved prognoses relative to the possible course the lesions in question may take.

As a general rule, it will be noticed that the papillomaviruses, although differing very much from each other, have molecular sizes of the order to 7,000–8,000 base pairs. In addition, their genomes do nonetheless exhibit certain degrees of homology. In what follows, reference will be mad to assessments of the percentages of homology between types and subtypes of papillomaviruses, these percentages of homology being derived from hybridization assays carried out under non-stringent conditions and, also, under stringent conditions.

Several types of papillomaviruses are distinguished by the percentages of homology measured under stringent conditions. It is said that the papillomaviruses which exhibit homologies of less than 50% under these conditions belong to different types. It will be noted in this respect that the percentages of homology between viruses of different types may even fall to zero under the said stringent conditions. Viruses for which percentages of homology higher than 50% are observed under these stringent conditions are considered to belong to the same type and may give rise to different subtypes within this same type.

The hybridization assays under non-stringent conditions involve placing in mutual contact DNAs derived from two isolates of virus under the conditions described by HEILMAN, C. A. et al. 1980, J. Virol, 36, 395–407, and CROISSANT et al,, 1982, C. R. Acad. Sci. Paris, 294, 581–586 (heteroduplex molecules).

Performance of hybridization assays under stringent conditions involves placing in mutual contact DNAs derived from two isolates of virus under the conditions described by KREMSDORF, D. et al. ((1982), J. Virol. 43, 436–447 and 1983, J. Virol., 48, 340–351) and DAVIS, R. W. et al., 1971, Methods Enzymol., 21, 413–418 (heteroduplex molecules).

Briefly, it will be noted that the papillomaviruses belonging to the same type possess hybridizable sequences having nucleotide sequences more or less identical over 80% to 100% of their respective, total lengths, whereas such homologous sequences can be reduced to 60% or even less in papillomaviruses of different types. The degree of identity or analogy of the sequences of papillomaviruses of different types which hybridize with each other under non-stringent conditions is obviously lower than in the case in which the papillomaviruses belong to the same type.

The study which the inventors have carried out has shown that both the degree of genetic heterogeneity between papillomaviruses of different types is greater than was hitherto considered to be the case and, at the same time, that the different types are often found associated with forms or variants of infections presenting a certain degree of specificity.

Consequently, the invention relates not only to DNAs prepared from the various new papillomaviruses which have been isolated and the probes which may be constituted by all or part of these DNAs, but also mixtures or "cocktails" of types of papillomaviruses which may be put to use for the more effective diagnosis of various types of infection, and even for the diagnosis of the level of risk which accompanies the discovery in a patient of specific types of papillomaviruses. The number of probes for papillomaviruses described in the present application to which may be added, if necessary, those composed of genomic DNAs of papillomaviruses which had already been isolated and their combination in defined mixtures, thus making it possible to perform more refined diagnoses, in particular, by enabling a clearer distinction to be made between the various types of infection and the various types of papillomavirus to which they may be ascribed, or the infections which are liable to develop as a result of the influence of such papillomaviruses, and, within a given class of specific infections, by providing a better diagnosis of the degree of risk of these infections being transformed into more serious diseases. For example, the aim of the invention is to provide agents which make it possible, in cases of infections manifesting themselves as cases of epidermodysplasia verruciformis, to assess more precisely the degree of risk that the latter will develop into epidermal cancers.

As a general rule and with the aim of simplifying the subsequent description, the entire genomes of papillomaviruses will be designated by the abbreviation "DNA-HPV".

With the same aim of simplifying the text in mind, reference is made in the subsequent discussion to diagrams in which the figures consist of restriction maps of the DNA-HPVs, which include, moreover, DNA-HPVs of papillomaviruses already known.

The restriction maps give the positions of the cleavage site of various restriction endonucleases. The origin of the maps is usually constituted by a unique cleavage site. The distances from the origin are expressed in percentages of the length of the genome. One map unit represents 1% of the length of the genome.

BRIEF DESCRIPTION OF THE DRAWINGS

FIG. 1 is a diagrammatic representation of the restriction maps for papillomaviruses HPV1a, HPV2d and HPV4a.

FIG. 9 is a diagrammatic representation of the restriction map for papillomavirus HPV-IP2.

FIG. 10 is a diagrammatic representation of the restriction map for papillomavirus HPV-IP4.

Figure 1:
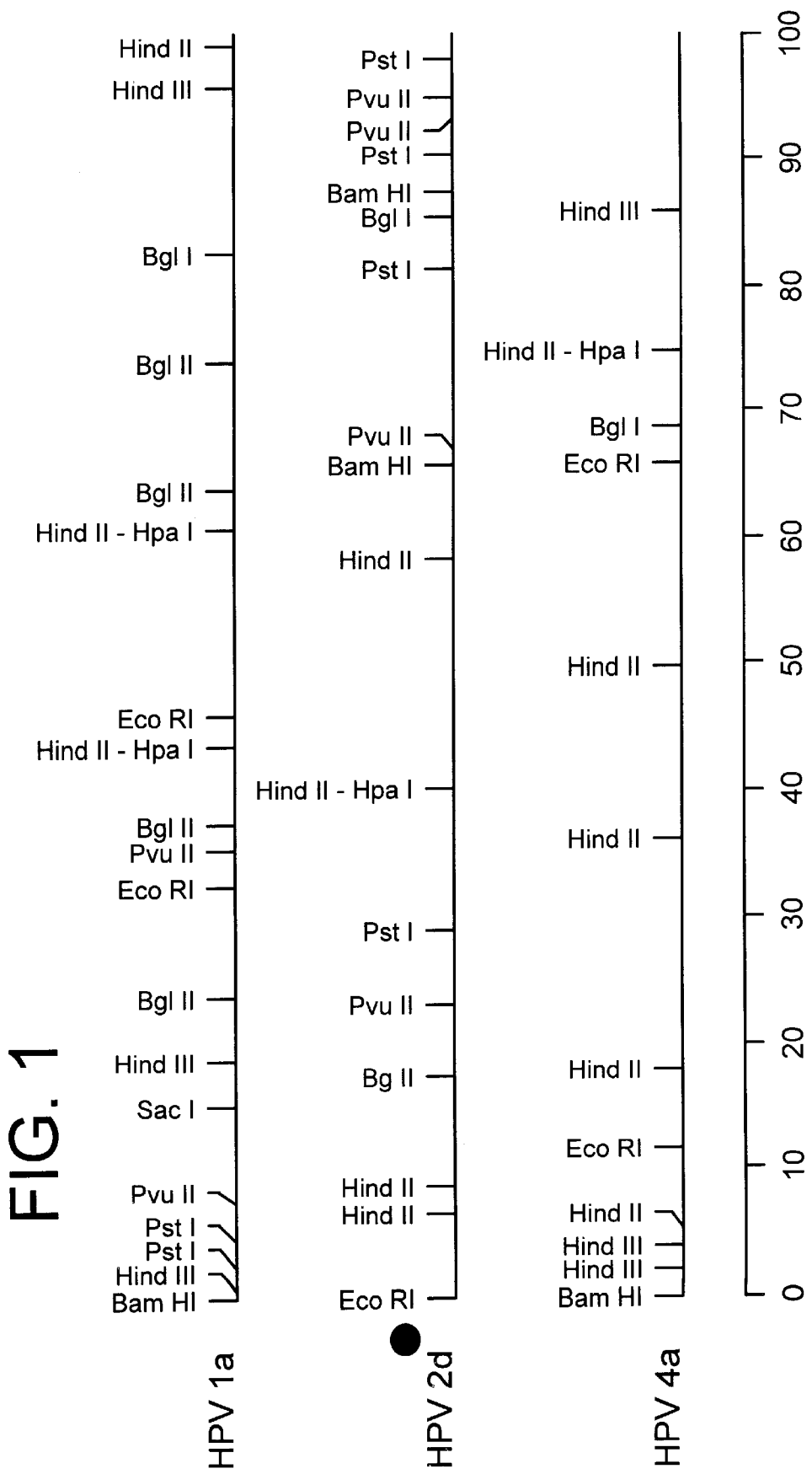
Figure 2:
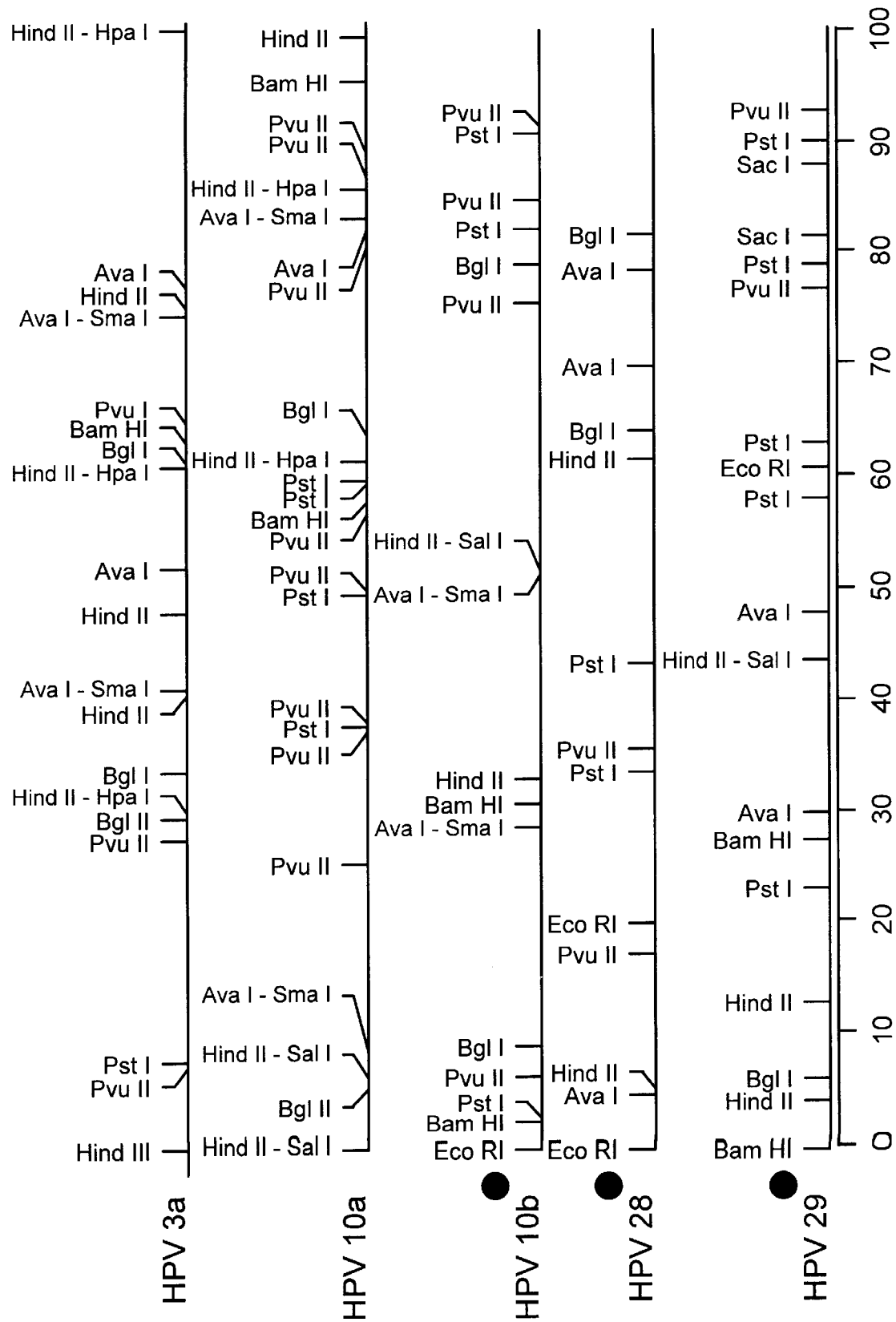
FIG. 2 is a diagrammatic representation of the restriction maps for papillomaviruses HPV3a, HPV10a, HPV10b, HPV28 and HPV29.
Figure 3:
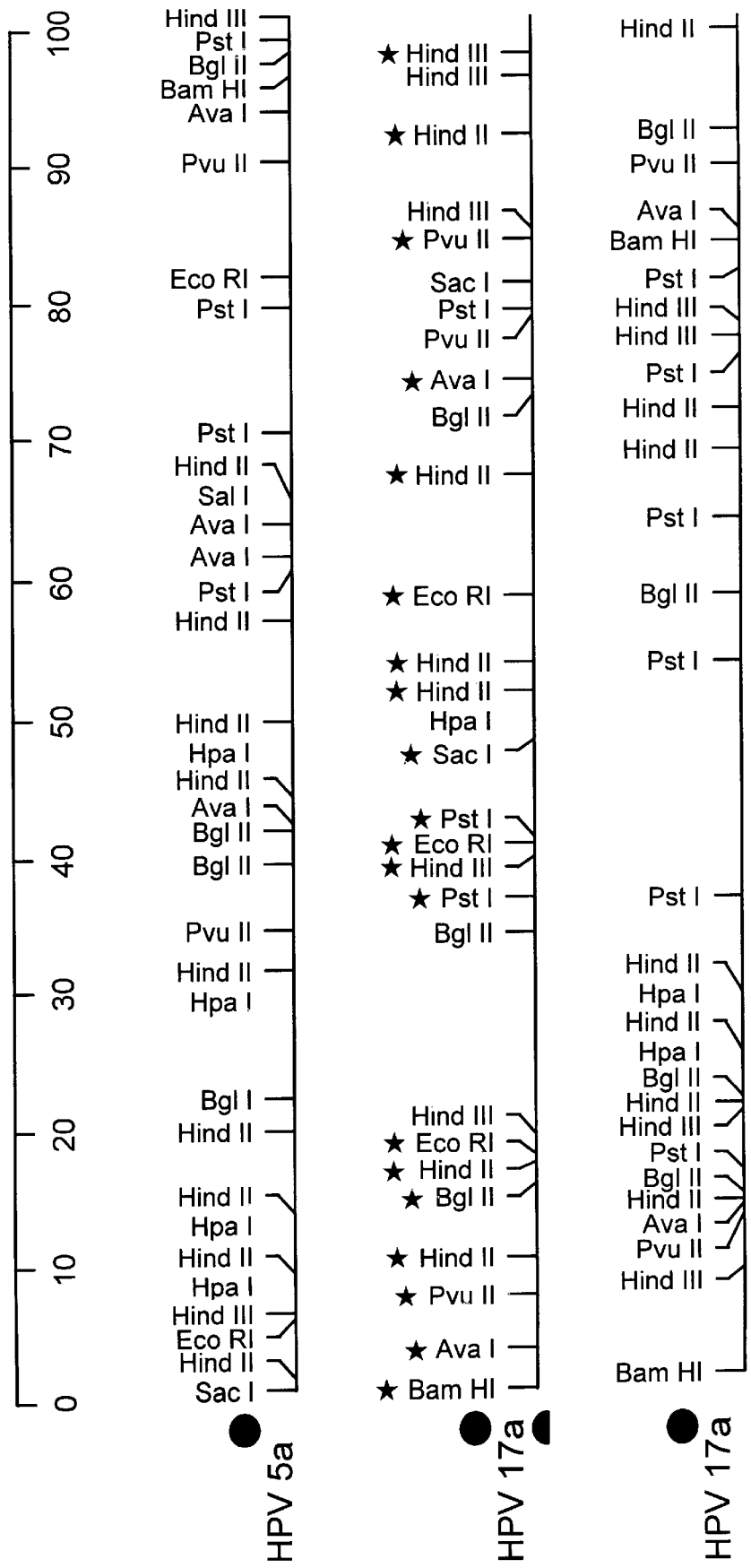
FIG. 3 is a diagrammatic representation of the restriction maps for papillomaviruses HPV5a, HPV17a, and HPV24.

In the first place, the invention relates more particularly to each of the DNA-HPVs chosen from among the totality of DNAs which possess molecular sizes varying between 7,000 and 8,000 base pairs and which, in respect of the DNA-HPVs obtained from papillomaviruses, are characterized by restriction maps which appear in the diagrams and which have been given the designations HPV-2d, HPV-10b, HPV-14a, HPV-14b, HPV-15, HPV-17a, HPV-17b, HPV-19, HPV-20, HPV-21, HPV-22, HPV-23, HPV-24, HPV-28, HPV-29, HPV-31 and HPV-32, HPV-IP2 and HPV-IP4.

It is obvious that the invention also extends its coverage to DNA-HPVs which can be considered as belonging to the same types as those which have just been mentioned.

The restriction maps corresponding to the DNA-HPVs of recently characterized viruses are indicated by a closed black circle. The invention also relates to the aforementioned DNA-HPV fragments or to fragments capable of hybridizing with these latter, in particular, under stringent conditions. Similarly, the invention relates to recombinant DNAs containing all or part of each of the DNA-HPVs cited above, and more especially to DNA recombinants containing fragments corresponding to the genes E1, E6–E7, L1 and L2 and also fragments containing sequences corresponding to the intergenic regions of the said DNA-HPVs. The invention finally relates to the probes which can be constituted from these respective DNA-HPVs or from corresponding fragments, and the in vitro diagnostic procedures in which these probes are used.

The preparations of viral DNA were extracted selectively (LUTZNER, M. A. et al., 1983, Lancet ii: 422–424) from material obtained by grattage of benign lesions in six European patients suffering from EV and in two South American patients suffering from EV. The DNAs of HPVs were purified by equilibrium centrifugation in cesium chloride gradients and/or sedimentation in sucrose gradients in the presence of ethidiumbromide, in accordance with experimental procedures previously described (the articles of KREMSDORF, et al. cited above and ORTH, G, et al. 1980, Cold Spring Harbor Conf. Cell Proliferation 7:259–282). The preparations of DNA were treated with restriction endonucleases and the digestion products were separated by electrophoresis from agarose gels (the articles by KREMSDORF et al. already cited). In addition to the HPV5, 8 and 12 (the articles by KREMSDORF et al. already cited) and HPV2 (HEILMAN, C. A. et al., 1980, J. Virol. 36:395–407 and ORTH, G. et al., 1980, Cold Spring Harbor Conf. Cell Proliferation 7:259–282) isolated from the verrucae of one of the patients, eleven strains have been identified which provide important models of cleavage of DNA by restriction enzymes, different from those which have been previously characterized. The new types of HPV have been assigned a number and the subtypes of a given type have been assigned the same number followed by a letter, denoting the chronological order of their identification (COGGIN, J. R. et al., Cancer Res. 39:545–546). The genomes of the 11 new HPVs have been cloned in *Escherichia coli* K12, strain C600 (article by KREMSDORF, D et al., (1983) already cited). The DNAs were inserted in the form of molecules of unit length with the exception of two fragments of the DNA of HPV24 produced by the endonuclease BamHI. They were inserted either into the plasmid pBR322 (SUTCLIFFE, J. G., 1978, Nucleic Acids Res. 5:2721–2728) by making use of the unique cleavage sites of AvaI, BamHI and HindIII, or into the recombinant plasmid which has integrated the HindIII B fragment of the DNA of HPV5 (article by KREMSDORF, D. et al., 1982, already cited) which contains a unique SacI site. More particularly, the HPV17b and 22 were inserted in the form of DNA molecules of unit lengths after being cleaved with an enzyme (SacI) which cleaves the HPV-DNA and the recombinant plasmid pBR322 containing the HindIII B fragment of the DNA or HPV5 only once. The DNA of HPV14a was inserted into the plasmid pBR322 in the form of a DNA molecule of unit length after partial digestion of the viral DNA preparation with HindIII, an enzyme which produces two fragments of 96.1% and 3.9% of the length of the genome. The BamHI A and B fragment of HPV24 (which have sizes corresponding to the numbers 83.1% and 16.9% of the length of the genome, respectively) were inserted separately into the plasmid pBR322.

Figure 4A:
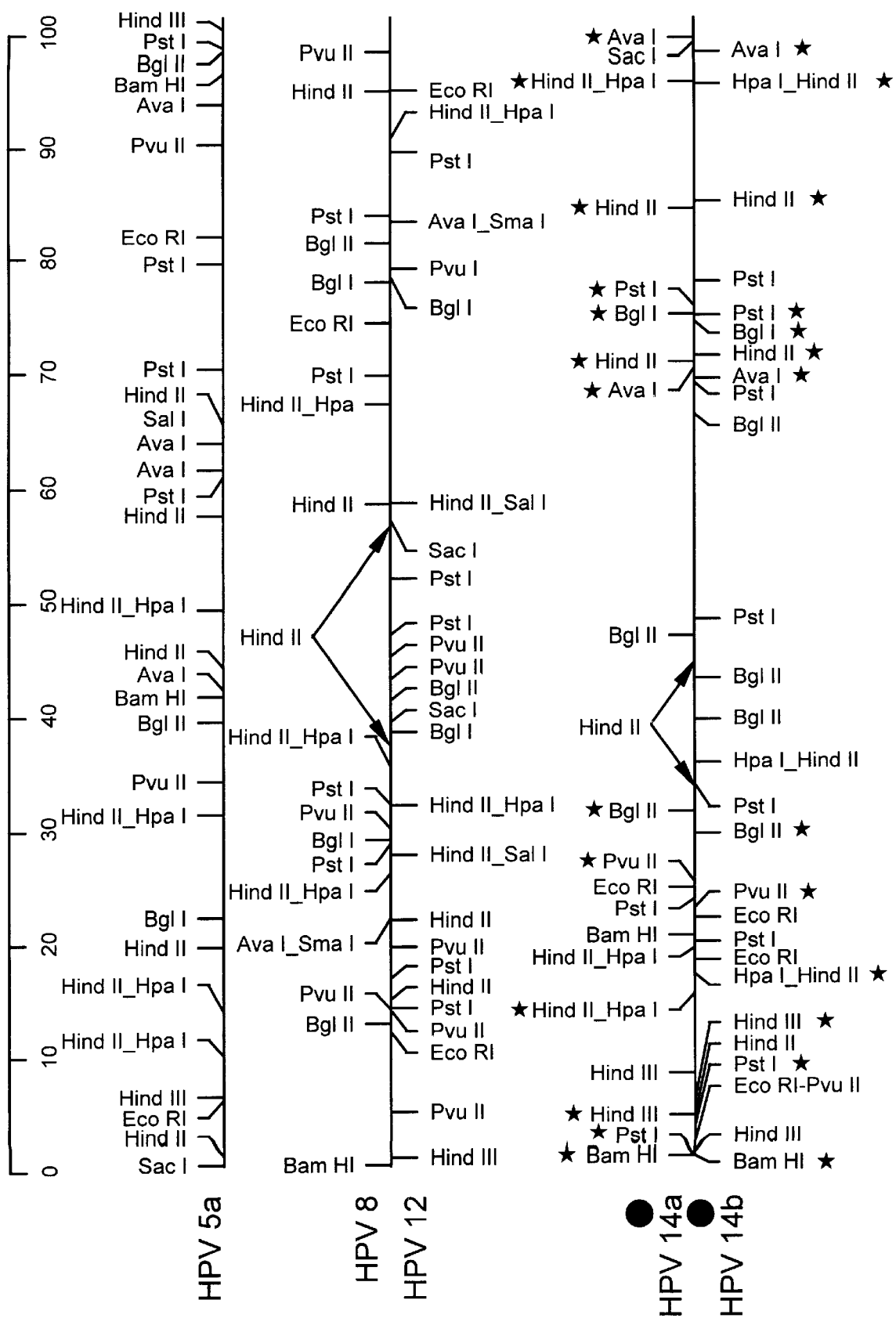
FIG. 4a is a diagrammatic representation of the restriction maps for papillomaviruses HPV5a, HPV8, HPV12, HPV14a, and HPV14b.
Figure 4B:
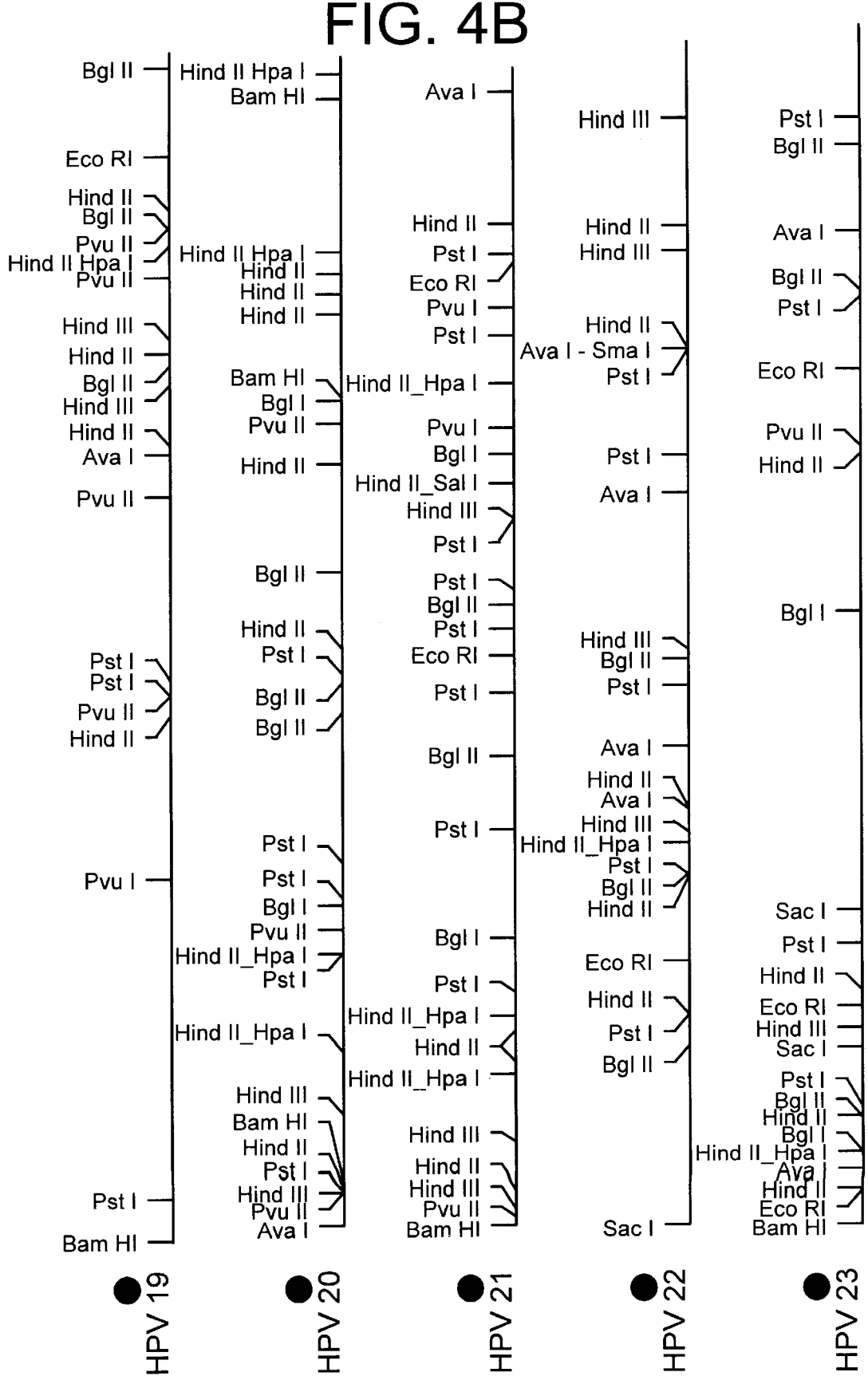
FIG. 4b is a diagrammatic representation of the restriction maps for papillomaviruses HPV19, HPV20, HPV21, HPV22, and HPV23
Figure 5:
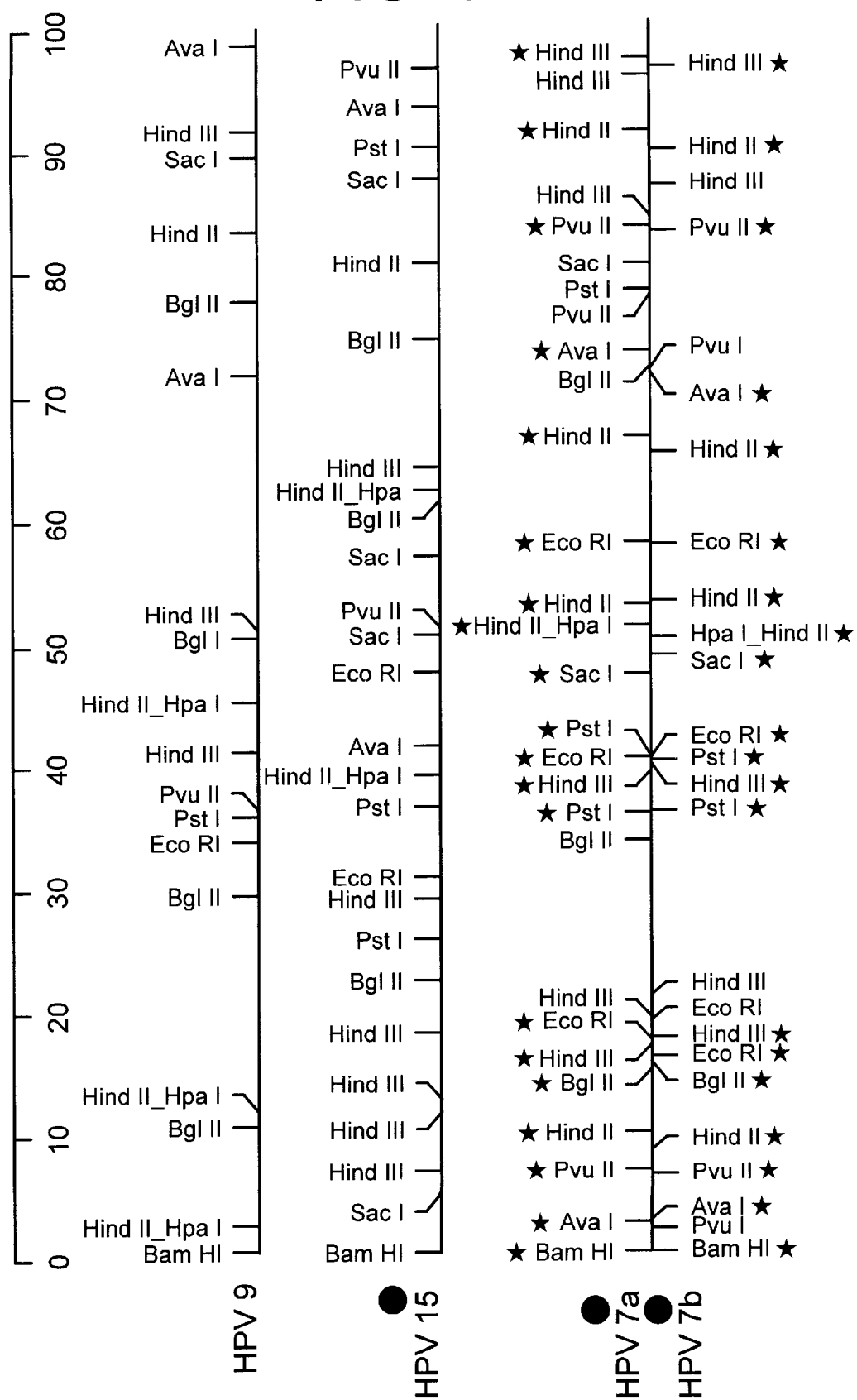
FIG. 5 is a diagrammatic representation of the restriction maps for papillomaviruses HPV9, HPV15, HPV7a, and HPV7b.
Figure 6:
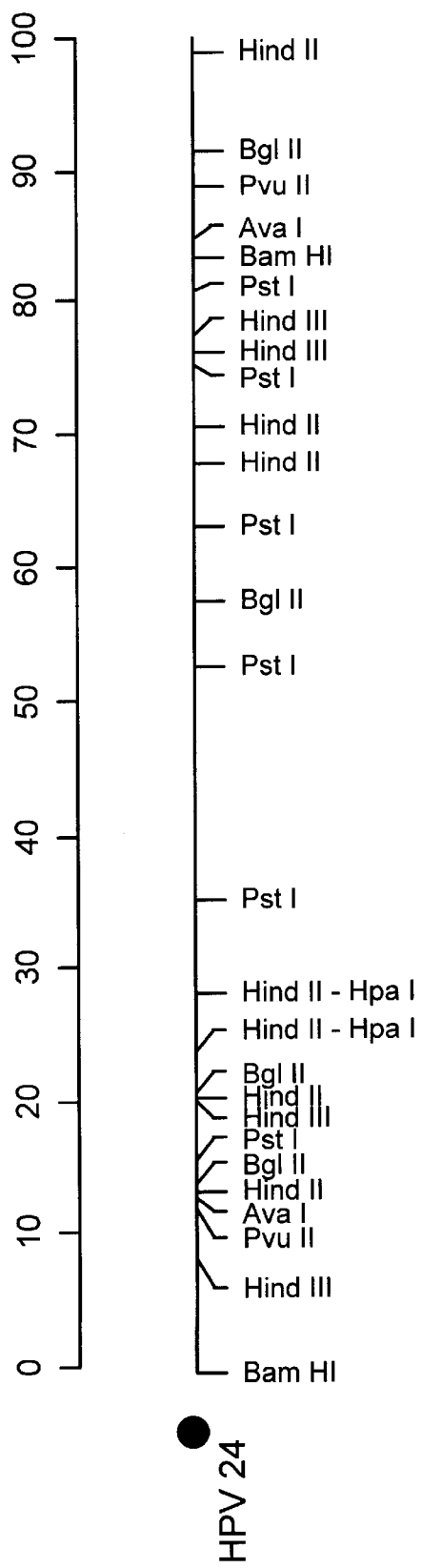
FIG. 6 is a diagrammatic representation of the restriction map for papillomavirus HPV24.
Figure 7:
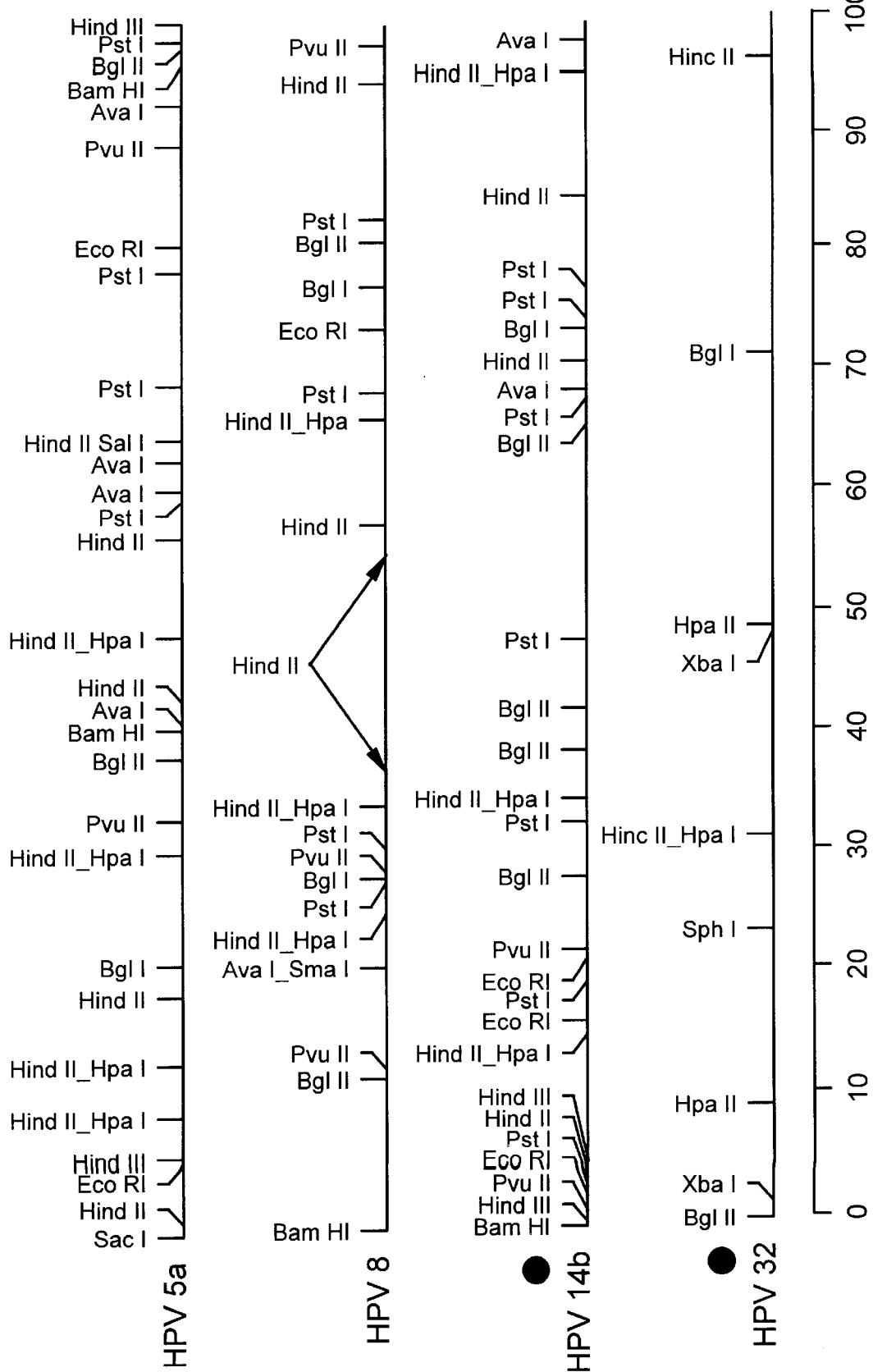
FIG. 7 is a diagrammatic representation of the restriction maps for papillomaviruses HPV5a, HPV8, HPV14b, and HPV32.
Figure 8:
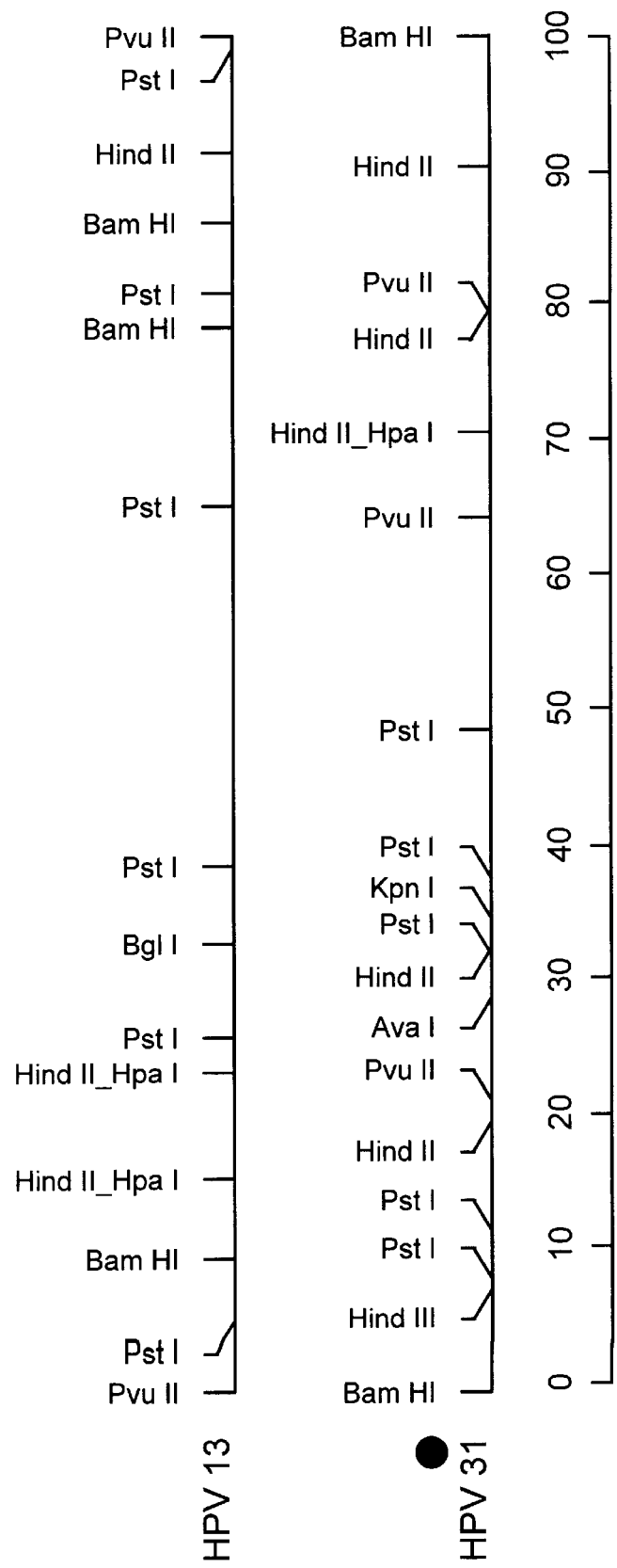
FIG. 8 is a diagrammatic representation of the restriction maps for papillomaviruses HPV13 and HPV31.

The clones isolated and the sources of the corresponding HPV are presented in Table I which follows:

obvious analogy was detected between these maps, with the exception of those of HPV14a and 14b, on the one hand (FIGS. 4a and 4b), and those of HPV17a and 17b, on the other (FIG. 5). Of the 21 and 31 sites localized on the DNAs of the HPV14a and 14b, respectively, 15 were found to be common to both when one of the two BamHI cleavage sites of the DNA of HPV14a was aligned with the unique BamHI cleavage site of the DNA of HPV14b. In a similar manner, 21 of the 29 cleavage sites situated on the DNA of HPV17a were also found to correspond to sites on the DNA of HPV17b (with 26 sites) when the unique BamHI cleavage sites were aligned.

No obvious analogy was detected between these maps and those previously established for the HPV associated with EV (HPV3a, 5, 8, 9, 10 and 12) (8, 9, 16, 18, 20), with cutaneous warts (HPV1, 2, 4 and 7), and with lesions to mucous membranes (HPV6b 11a, 13 and 16) (1, 33, 19), with the exception of the map of HPV14a which is closely related to the map of an HPV isolated from a Japanese patient suffer-

TABLE I

ORIGIN OF THE CLONED HPV-DNAs.

| Patient[a] | Nationality | Source[b] | Type of HPV-DNA | | Other types of HPV found in the patients |
|---|---|---|---|---|---|
| | | | cloned | Cloning enzyme[c] | |
| 1 | Polish | warts; knees | 14a | Hind III | 5 |
| | | | 15 | Bam HI | |
| 2 | French | warts; hands | 14b | Bam HI | |
| 3 | Colombian | maculae; trunk | 17a | Bam HI | 5 |
| 4 | Italian | maculae; chest | 17b | Sao I | 5 |
| | | | 22 | Sao I | |
| 5 | Dutch | maculae; back | 19 | Bam HI | 5, 8, 17a |
| | | maculae; chest | 24 | Bam HI | |
| 6 | Colombian | warts; hands | 20 | Ava I | 5, 8, 24 |
| 7 | Polish | warts; knees | 21 | Bam HI | 2, 12, 17a, 20 |
| 8 | Polish | maculae; forearm | 23 | Bam HI | 5, 8, 20 |

In order to identify the recombinant plasmids the electrophoretic mobilities of the digestion products of the recombinant DNAs and the non-cloned HPV-DNAs were compared after treatment with a mixture of two restriction endonueleases containing the endonuclease utilized to insert the viral sequences into the plasmid. The number and the molecular size of the isolated fragments indicated that the entire viral genomes had been integrated in each case. Size heterogeneity of the DNAs was observed when the DNAs of the HPVs non-cloned or excised from the plasmid sequences, were analysed by electrophoresis on agarose gel (data not presented). The DNAs of HPV14b, 19, 20 and 21 have sizes similar to those of HPV3a, 5, 8 and 12 (about 7,700 nucleotide pairs) (articles by KREMSDORF, D. already cited), whereas the DNAs of HPV15, 17a, 17b, 22 and 23 are somewhat less like that of HPV9 (about 7,200 nucleotide pairs) (articles by KREMSDORF, D., 1982 and ORTH, G., 1980, already cited).

The sensitivity of the cloned viral genomes to 14 restriction endonucleases has been analysed and the corresponding restriction maps have been established (FIGS. 1 to 10). The restriction maps of some of the HPV-DNAs are reproduced in some of the figures for reasons which will be explained later. Between 22 and 33 cleavage sites have been localized by means of the methods previously described (9). No ing from EV (24), This latter isolate differs from HPV14a by two additional cleavage sites, one for BamHI and the other for HindIII, whereas the locations of the AvaI, BamHI, BglI, EcoRI, HindII and HindIII sites are similar for the two viruses. Cross-hybridization experiments have confirmed that these two viruses are very closely related.

It will also be noticed that some sites (those indicated by the arrows) have not been localized. Cleavage sites which differ in their location by less than 2% of the length of the genome are considered to be conserved (✻) The enzymes which did not give rise to any cleavage were: PvuI, SalI and SmaI for the DNAs of HPV14a and 23; PvuI, SacI, SalI and SmaI for the DNA of HPV14b; BglI, PvuI, SalI and SmaI for the DNAs of HPVI5, 17a and 17b; BglI, SacI, SalI and SmaI for the DNA of HPV19; EcoRI, PvuI, SacI and SmaI for the DNA of HPV20; SacI and SmaI for the DNA of HPV21; BamHI, BglI, PvuI, PvuII and SalI for the DNA of HPV22; BglI, EcoRI, PvuI, SacI SalI and SmaI for the DNA of HPV24.

The existence of sequence homology between DNAs of recently characterized HPV as well as between these latter and the DNAs of the HPV of EV previously characterized (HPV3a, 5, 8, 9, 10 and 12), of the HPV associated with dermalwarts (HPV1, 2, 4 and 7), and of HPV associated with lesions to mucous membranes (HPV6b, 11a, 13 and 16) has been studied. Hybridization experiments by fixation on filter paper and DNA—DNA hybridization in liquid phase at saturation followed by digestion with the nuclease S1 were carried out under the stringent conditions previously described (8, 9). In particular, the HPV-DNAs were labelled by "nick-translation" and fractionated by sedimentation in alkaline sucrose gradients (as numbers 5% to 20%) as previously described (13). HPV-DNAs (4,000 cpm) were incubated in 0.48 M NaCl—1 mM EDTA (pH 6.8) at 68° C., in the presence of either DNA of calf thymus (20 µg) or non-labelled HPV-DNA (0.20 µg) as previously described (8, 9) The specific activities of the HPV-DNA probes varied between $5.3 \times 10^7$ and $2 \times 10^8$ cpm/µg. The percentage of hybridization was determined by measuring the fractions resistant to the nuclease S1. The numbers represent the values corrected for the spontaneous auto-renaturation of the probes (4% to 15%) and normalized to 100% for homologous hybridization (75% to 95%). The abbreviation ND means not determined. The relative extent of cross-hybridizations between the HPV-DNAs under the conditions mentioned above are expressed as a percentage of hybridization between a labelled HPV-DNA and an unlabelled HPV-DNA.

8, 9, 10 and 12), with the exception of the HPV14a and 14b, on the one hand, and the HPV17a and 17b, on the other, which showed considerable cross-hybridization. These observations justify the classification of the new viruses into nine new types (HPV14, 15, 17, 19, 20, 21, 22, 23 and 24) plus two subtypes of the types 14 (HPV14a and b) and 17 (HPV17a and b).

Similarly, the various HPVs were classified in groups on the basis of their sequence homology (or absence of sequence homology) under stringent conditions of molecular hybridization. These groups, designated by the letters A to H, are listed in Table III which follows. This table indicates the diseases which were diagnosed in the carriers of these HPVs (in isolation or in combination) and the oncogenic potential which is ascribed to each of them.

The DNAs of the HPV5, 8, 12, 14, 19, 20, 21, 22 and 23 exhibit degrees of cross-hybridization (group homologies) varying from 5% to 38%, and exhibit a noteworthy degree of cross-hybridization (4% to 13%) only with the DNAs of the HPV5, 8 and 12. Thus, these viruses form part of a group of HPV of EV previously defined (9).

Similarly, the DNAs of the HPV9, 15 and 17, which display among themselves a cross-hybridization of about 20% and a cross-hybridization of about 6% with the DNA of

TABLE 2

DEGREE OF CROSS-HYBRIDIZATION BETWEEN THE HPV-DNAs DETERMINED IN SOUTION

| Unlabelled HPV-DNA | % hybridization with $^{32}$P-labelled HPV-DNA | | | | | | | | | | | | |
|---|---|---|---|---|---|---|---|---|---|---|---|---|---|
| | 3a | 5 | 14a | 14b | 19 | 20 | 21 | 22 | 21 | 15 | 17a | 17b | 24 |
| 1a | 0.1 | 0.3 | 0.2 | 0.3 | 0 | 0.8 | 2.9 | 0 | 0 | 1.0 | 0.4 | 0.2 | 0 | 0 |
| 11a | 1.6 | 1.0 | 1.3 | 0 | 0.3 | 0.1 | 0.7 | 3.7 | 0 | 0.1 | 0.1 | 0.6 | 3.3 | 0 |
| 3a | 100 | 1.8 | 1.0 | 0 | 1.5 | 0.1 | 1.5 | 0 | 1.9 | 0.1 | 1.7 | 1.2 | 1.8 | 3.0 |
| 10 | 32.3 | ND | ND | 0.1 | 0 | 0.1 | 1.9 | 3.0 | ND | 0 | 1.6 | 0.1 | 2.0 | ND |
| 5 | 0.2 | 100 | 12.1 | 12.4 | 5.8 | 9.3 | 9.4 | 10.1 | 5.8 | 4.3 | 0.7 | 3.6 | 0 | 2.4 |
| 8 | 1.1 | 15.7 | 9.9 | 13.4 | 8.5 | 5.6 | 5.0 | 7.1 | 5.8 | 3.5 | 1.5 | 3.2 | 3.8 | 0.1 |
| 12 | 0.1 | 19.3 | 9.2 | 12.5 | 5.3 | 8.6 | 9.3 | 11.7 | 4.0 | 3.6 | 1.2 | 0.1 | 1.9 | 0 |
| 14a | 0.2 | 13.2 | 100 | 88.8 | 14.6 | 12.4 | 32.9 | 10.1 | 24.6 | 3.0 | 2.2 | 2.4 | 4.1 | ND |
| 14b | ND | 10.5 | 94.1 | 100 | 9.1 | 28.4 | 35.4 | 9.5 | 28.2 | 0 | 0 | 0 | 0 | 0 |
| 19 | ND | 7.2 | 21.4 | 20.6 | 100 | 7.6 | 8.8 | 15.5 | 27.7 | 0 | 0 | 0 | 2.2 | 1.0 |
| 20 | ND | 9.9 | 28.8 | 37.9 | 6.2 | 100 | 25.4 | 13.7 | 14.1 | 0 | 0 | 2.1 | 0 | 3.6 |
| 21 | ND | 10.5 | 38.7 | 40.5 | 6.4 | 37.5 | 100 | 9.8 | 18.6 | 0.1 | 0 | 2.5 | 0.3 | 0 |
| 22 | ND | 7.2 | 7.4 | ND | 17.3 | 7.2 | 10.8 | 100 | 17.9 | 0 | 0 | 0.1 | 0.1 | 0 |
| 23 | ND | ND | ND | ND | ND | ND | ND | 21.2 | 100 | 0 | 0.5 | 0 | 0 | 0.1 |
| 9 | 0.4 | 3.1 | 0.5 | 1.2 | 0 | 2.0 | 1.0 | 0 | 0 | 100 | 5.5 | 6.3 | 5.4 | 0 |
| 15 | 0.4 | 3.3 | 2.1 | 3.3 | 0 | 0.1 | 0.8 | 0 | 0 | 7.8 | 100 | 22.5 | 21.6 | 0 |
| 17a | 0.7 | 1.2 | 1.4 | 2.8 | 0 | 0.1 | 0.1 | 0.8 | 1.4 | 7.6 | 19.5 | 100 | 92.7 | 0 |
| 17b | ND | ND | ND | 1.4 | 0 | 0.3 | 3.4 | ND | ND | ND | ND | 86.3 | 100 | ND |
| 24 | ND | ND | 0.1 | 2.6 | ND | ND | ND | 0.8 | 0 | 0.2 | 0 | 1.1 | 1.1 | 100 |

It will be noted that there is an absence or virtual absence of cross-hybridization between the genomes of HPV1, 2, 4, 6b, 7 and 11a and the DNAs of the newly cloned HPV of EV labelled with P or between DNAs of non-labelled HPV of EV and specific probes for HPV13, 16 and 18. Similarly, no or virtually no cross-hybridization was detected between the DNAs of the HPV14a, 14b, 15, 17a, 17b, 19, 20, 21, 22, 23 and 24 and the DNAs of the HPV1a and 11a by reassociation at saturation (Table 2). The newly cloned HPV-DNAs showed no or virtually no cross-hybridization or a cross-hybrization of less than 50% among themselves and with the genomes of the other HPV associated with EV (HPV3a, 5, HPV9, also belong to a group of HPV of EV already described (9). The HPVs types 13 and 31 may be considered as belonging to the same group. Finally, the HPVs types 1, 2, 4, 24 and 32, which exhibit almost no homology with the genomes of the other HPV are considered to represent the first numbers of other groups, distinct from each other and from the groups already known.

The invention also relates more especially to fragments of DNA, derived from the above-mentioned HPV-DNAs, and more particularly to

TABLE III

CLASSIFICATION OF THE HPV WHICH ARE THE SUBJECT OF THE PATENT APPLICATION ACCORDING TO THE DEGREE OF HOMOLOGY OF THEIR NUCLEOTIDE SEQUENCE DETERMINED BY MOLECULAR HYBRIDIZATION UNDER STRINGENT CONDITIONS

| Group[1] | Types[2] of HPV | Homologies within the group | Associated diseases | Oncogenic potential | Mixture of probes |
|---|---|---|---|---|---|
| A | 1 | | myrmecias | very weak | 1 |
| B | 2 | | verrucae | weak | 1 |
| C | 3, 10, 28*, 29* | 14 à 38% | plane warts intermediate warts actinic keratoses Bowen's disease | moderate a related virus, associated with intra-epithelial neoplasias and and cutaneous cancers, characterization pending | 2 |
| D | 4 | | verrucae | very weak | 1 |
| E | 5, 8, 12, 14* 19*, 20*, 21*, 22*, 23* | 4 à 38% | epidermodysplasia verruci. actinic keratoses Bowen's disease cutaneous carcinomas | HPV5, 8 and 14 associated with EV carcinomas; a related virus, associated with intra-epithelial neoplasias and cutaneous cancers, characterization pending | 3, 4, 7 |
| F | 9, 15*, 17* | 6 à 23% | Epidermodysplasia verruciformis | | 5 |
| G | 24* | | Epidermodysplasia verruciformis | | 6 |
| H | 13, 31* | | Oral epithelial hyperplasia. Oral leucoplasias | | 8 |
| I | 32* | | Bowen's disease | cutaneous intra-epithelial neoplasias | 7, 9 |

[1]The genomes of the HPV types belonging to different groups usually do not show detectable sequence homology under stringent conditions of molecular hybridization. The genomes of the HPV types belonging to the same group show a sequence homology of less than 50%.
[2]The new HPV types are indicated by an asterisk.

those corresponding to the genes E6–E7; E1; L2; L1 and to their inter-genic regions. The relative position and length of these various fragments with respect to the sites taken as origins (FIGS. 1 to 9) are indicated in Table IV which follows:

map and the genetic map of HPV6b (E. Schwarz et al, EMBO J., 1983, 2, 2341–2348), after analysis in the electron microscope of heteroduplex molecules formed under stringent (Tm −29° C.) or less stringent (Tm −40° C.) conditions of hybridization. The physical maps of HPV10b, 28 and 29

TABLE IV

PUTATIVE LOCALIZATION OF THE PRINCIPAL GENES AND OF THE INTERGENIC REGION ON THE PHYSICAL MAPS OF THE HPV GENOMES

| | Co-ordinates of the 5' and 3' ends of the fragments corresponding to genes | | | | |
|---|---|---|---|---|---|
| HPV type | E6 - E7 | E1 | L2 | L1 | the intergenic region |
| 1 | 44 - 34.5 | 35 - 11 | 95 - 75.5 | 76.5 - 56 | 56 - 44.5 |
| 3 | 18.5 - 9 | 9.5 - 85.5 | 69.5 - 50 | 51 - 30.5 | 30.5 - 19 |
| 5 | 6.5 - 97 | 97.5 - 73.5 | 57.5 - 38 | 39 - 18.5 | 18.5 - 7 |
| 8 | 63 - 53.5 | 54 - 30 | 14 - 94.5 | 95.5 - 75 | 75 - 63.5 |
| 9 | 42 - 32.5 | 33 - 9 | 93 - 73.5 | 74.5 - 54 | 54 - 42.5 |
| 10a | 49 - 39.5 | 40 - 16 | 0 - 80.5 | 81.5 - 61 | 61 - 49.5 |
| 10b | 93 - 83.5 | 84 - 60 | 44 - 24.5 | 25.5 - 5 | 5 - 93.5 |
| 12 | 23.5 - 14 | 14.5 - 90.5 | 74.5 - 55 | 56 - 35.5 | 35.5 - 24 |
| 14 | 8.5 - 99 | 99.5 - 75.5 | 59.5 - 40 | 41 - 20.5 | 20.5 - 9 |
| 15 | 39.5 - 30 | 30.5 - 6.5 | 90.5 - 71 | 72 - 51.5 | 51.5 - 40 |
| 17 | 46 - 36.5 | 37 - 13 | 97 - 77.5 | 78.5 - 58 | 58 - 46.5 |
| 24 | 24.5 - 15 | 15.5 - 91.5 | 75.5 - 56 | 57 - 36.5 | 36.5 - 25 |
| 28 | 47.5 - 38 | 38.5 - 14.5 | 98.5 - 79 | 80 - 59.5 | 59.5 - 48 |
| 29 | 89.5 - 80 | 80.5 - 56.5 | 40.5 - 21 | 22 - 1.5 | 1.5 - 90 |
| 31 | 89 - 78.5 | 80 - 53.5 | 33.5 - 15.5 | 17.5 - 96.5 | 96.5 - 92.5 |

The localization of the genes on the genome of HPV1 was deduced from the nucleotide sequence of this genome (Patent O. Danos, M. Katinka and M. Yaniv). The physical maps of the genomes of the HPV3, 5, 8, 9, 10a, 12, 14, 15, 17 and 24 were aligned with the physical map and the genetic map of HPV1, and that of HPV31 with the physical map and the genetic map of HPV6b (E. Schwarz et al, EMBO J., 1983, 2, 2341–2348), after analysis in the electron microscope of heteroduplex molecules formed under stringent (Tm −29° C.) or less stringent (Tm −40° C.) conditions of hybridization. The physical maps of HPV10b, 28 and 29 were aligned with the physical maps of HPV3a and 10a after the conserved sites for restriction enzymes had been juxtaposed.

The values of the co-ordinates reported in Table IV show the position on the physical maps presented in the FIGS. 1–9 of the 5' and 3' ends of the segments of the homologous genomes of the genes E6 and E7, E1, L2 and L1 and of the intergenic region with respect to the genome of HPV1a or, in the case of HPV31, with respect to the genome of HPV6b.

The intergenic region (comprising the elements concerned with regulation) and the adjacent genes E6 and E7 (which probably correspond to the principle transformation genes expressed in tumours do not show any sequence homology between genomes of HPV types belonging to different groups which is detectable by analysis in the electron microscope of heteroduplex molecules formed under non-stringent conditions of hybridization, or with genomes of most of the HPV types belonging to the same group when heteroduplex molecules formed under stringent conditions are similarly analysed. The E1 gene (implicated mainly in the replication of the viral DNA) and the L1 gene (coding for the major protein of the viral capsid which bears the principal antigenic determinants of the virions) do present sequence homologies between genomes of HPV types belonging to different groups which are detectable by analysis of heteroduplex molecules formed under non-stringent conditions of hybridization, and between genomes of HPV belonging to the same group when heteroduplex molecules formed under stringent conditions of hybridization are similarly analysed.

Probes prepared from recombinant plasmids containing the E1 and L1 regions can theoretically be used to detect the largest number of HPV types by molecular hybridization experiments carried out under either stringent or non-stringent conditions. Probes prepared from recombinant plasmids comprising the intergenic region or the E6 and E7 genes may be used to specifically detect one type of HPV or closely related HPV types.

The L2 region (which codes for a minor component of the viral capsid) displays a variable degree of conservation of nucleotide sequences among the different HPV types.

In the discussion which follows more precise descriptions of the conditions under which the viruses HPV-IP2 and HPV-IP4 were isolated will be given, and these will be followed by a description of the conditions under which the HPV-DNAs were isolated from these viruses.

Molecular cloning and characterization of a novel type of HPV associated with neoplasias and genital cancers (HPV IP2)

The presence of a new type of HPV was demonstrated in the DNA extracted from a cancer of the uterine cervix by hybridization with a radioactive probe specific for HPV type 16 under non-stringent conditions. No cross-hybridization was detectable when the hybridization was carried out under stringent conditions of hybridization. A study of the sensitivity of the DNA of this HPV to several restriction enzymes showed that the enzyme BglII cleaves the viral DNA at a unique site. After digestion of the DNA extracted from the tumour with endonuclease BglII, the fraction containing the DNA molecule of 8 kb (the size of a papillomavirus genome) was purified by centrifugation in a sucrose gradient. The molecules of 8 kb were inserted at the BglII site into a vector constituted by the plasmid PL15.5 (which contains a unique cleavage site for BglII and BamHI) which was inserted through its BamHI site into the DNA of the bacteriophage lambda L47.1. After encapsidation of the recombinant DNA and infection of host bacteria (*Escherichia coli*, strain LA101), the lysis plaques corresponding to recombinant phages were detected by Southern hybridization of the infected bacterial cultures using a radioactive DNA of HPV16 under non-stringent conditions. Several recombinant bacteriophages containing the totality of the viral sequences were isolated: cleavage of the phage DNA by the restriction enzyme BglII leads to an 8 kb fragment which hybridizes with the HPV16 probe under non-stringent conditions; cleavage of the DNA of the recombinant phages and the DNA of the original tumour by a mixture of the enzymes BglII and PstI gives rise to the same 5 fragments, the sum of the molecular weights of which is equal to the molecular weight of the papillomavirus genome. The DNA of the novel HPV was excised from the DNA of the recombinant bacteriophages, purified by electroelution, and recloned in the plasmid PL15.5. A restriction map of the viral DNA was constructed on the basis of the sensitivity of this DNA to 18 restriction endonucleases the action of which led directly to the identification of 21 cleavage sites (FIG. 9). The map thus established was different from the map of the genomes of the HPV identified up to now. The sequence homology between the DNA of the novel HPV and the DNA of the HPV so far identified was analysed by Southern hybridization experiments carried out under stringent conditions. The homology detected was always less than 5%, the greatest homology being detected with the genome of HPV16. The new virus, which was characterized from a cancer of the uterine cervix, thus constitutes a new type of HPV, provisionally named HPV-IP2.

The electron microscopic analysis of heteroduplex molecules formed under different conditions between the DNA of HPV-IP2 and the DNA of HPV1 has made it possible to align the physical maps of these two genomes and to define the theoretical position of the different genes carried by the DNA of the HPV-IP2.

PUTATIVE LOCALIZATION OF THE PRINCIPAL GENES AND THE INTRAGENIC REGION OF HPV-IP2 ON THE MAP OF THIS GENOME

|  | Co-ordinates of the ends | |
|---|---|---|
|  | 5' | 3' |
| E6-E7 | 62 | 71.5 |
| E1 | 71 | 95 |
| E2 | 95.5 | 11.5 |
| L2 | 11 | 30.5 |
| L1 | 31.5 | 52 |
| Intergenic region | 52 | 63.5 |

The use of radioactive probes prepared from the purified DNA of HPV-IP2 has enabled the pathogenicity of these viruses to be determined. The presence of the DNA of HPV-IP2 was demonstrated in one case of bowenoid papules of the external genital organs out of the 14 cases studied, in two invasive cancers of the uterine cervix out of 51 cases studied and in one case of intra-epithelial neoplasia of the uterine cervix out of 28 cases studied. Thus, HPV-IP2 represents a HPV type showing genital tropism and displaying oncogenic potential, the frequency of which is somewhat less than that of HPV18, and markedly less than that of HPV16. It is necessary to incorporate it in all mixtures of HPV-DNA intended for the preparation of molecular probes with a view to the diagnosis or screening of HPV types consituting a risk of developing into genital neoplasias and, in particular, cancers of the uterine cervix.

Molecular cloning and characterization of a novel type of HPV associated with precancerous lesions of the skin (HPV-IP4).

A novel type of HPV was demonstrated in the DNA extracted from a biopsy of actinic keratosis, a precancerous skin lesion, by molecular hybridization with a mixture of radioactive probes specific for the HPV types 5, 8 and 14 under stringent conditions. No cross-hybridization was detected when the hybridization was carried out with probes specific for the types 1, 2, 3, 7, 10, 13, 16, 18, 28, IP1 (previously known as HPV31), IP2 and IP3 (previously known as HPV32).

A study of the sensitivity of the DNA of this HPV to several restriction enzymes has shown that the enzyme EcoRI cleaves the viral DNA once. After digestion of the DNA extracted from the biopsy from the endonuclease EcoRI, the fraction containing the DNA molecules of 8 kb (corresponding to the size of the papillomavirus genome) was purified by centrifugation in a sucrose gradient. The 8 kb molecules were inserted at the EcoRI site into the DNA of the bacteriophage λgt wes λB. After encapsidation of the recombinant DNA and infection of host bacteria (*Escherichia coli*, strain LA101), the lysis plaques corresponding to recombinant phages were detected by Southern hybridization of the infected bacterial cultures using a mixture of the radioactive DNAs of HPV5, 8 and 14 under non-stringent conditions. Several recombinant bacteriophages containing the totality of the viral sequences were isolated: cleavage of the phage DNA by the restriction enzyme EcoRI gives rise to an 8 kb fragment which hybridizes with the probe specific for HPV5, 8 and 14 under non-stringent conditions; cleavage of the DNA of the recombinant phages and the DNA from the original lesion by a mixture of the enzymes EcoRI and PstI gives rise to the same six fragments, the sum of the molecular weights of which is equal to the molecular weight of the papillomavirus genome. The DNA of the novel HPV was excised from the DNA of a recombinant bacteriophage, purified by electroelution, and recloned in the plasmide pSP65. A restriction map of the viral DNA was constructed on the basis of the sensitivity of this DNA to 15 restriction endonucleases, the action of which led directly to the identification of 23 cleavage sites (FIG. 10). The map thus established is different from the map of the genomes of the HPVs identified up to now. The sequence homology between the DNA of the novel HPV and the DNA of the HPVs so far identified was analysed by Southern hybridization experiments carried out under stringent conditions. A homology of less than 50% was detected between the DNA of the novel HPV and the DNA of certain types of HPV previously identified in lesions of epidermodysplasia verruciformis (HPV5, 8, 12, 14, 19, 20, 21 and 25), but no homology was detected with the other types of HPV. The new virus characterized from an actinic keratosis isolate thus constitutes a new type of HPV, provisonally referred to as HPV-IP4.

The use of a radioactive probe prepared from the purified DNA of HPV-IP4 has led to the demonstration of the presence of HPV-IP4 in 42% of 17 patients studied who were suffering from epidermodysplasia verruciformis and in biopsies of actinic keratosis analysed. In view of its high frequency in patients suffering from epidermodysplasia verruciformis, a disease characterized by the frequent development of skin cancers, and as a consequence of its association with a fraction of actinic keratosis lesions which are considered to be precursors of squamous cell carcinoma of the skin, HPV-IP4 constitutes a type of HPV showing dermal tropism and displaying oncogenic potential. It is necessary to incorporate it in all mixtures of HPV-DNA intended for the preparation of molecular probes with a view to the diagnosis or screening of types of HPV constituting risk of developing into cancerous or precancerous lesions of the skin.

The invention also relates more especially to mixtures or cocktails of different HPV-DNAs (or probes containing such HPV-DNAs or fragments of the latter), combinations which can be used to carry out comprehensive diagnoses of different forms of papillomavirus infections, the ultimate aim of which is to provide a prognosis of the possible course the infection will take. Preferred mixtures in accordance with the infection are presented in Table V which follows.

This table also indicates the natures of the diseases most likely to be diagnosed by the use of the mixtures appearing at the left-hand side of the table. It will be noted that the groups in which the restriction maps are presented in the accompanying FIGS. 1–9 correspond to those of the viral types indicated in the column "Constitution" of Table V. This is also the reason which has led to some of the probes being reproduced several times in different figures of the appendices.

Each of these mixtures may also be defined as comprising at least one of the novel probes according to the invention. In other words, the mixtures for diagnosis according to the invention may be defined as containing:

1) at least the DNA of HPV2d, 2) at least one of the DNAs of HPV10b, 28 and 29, 3) at least one of the DNAs of HPV17, 24, 4) at least one of the DNAs of HPV14, 15, 17, 19, 20, 21, 22 and 23, 5) at least one of the DNAs of HPV15 and 17, 6) the DNA of HPV24, 7) the DNA of HPV14, 32, 8) the DNA of HPV31, 9) the DNA of HPV32, it being understood that the DNAs of the nine groups are chosen in a manner so as to be different from each other under all circumstances.

Given the great variety of HPVs which are likely to be isolated from different forms of warts or other mucosal or cutaneous lesions, it is preferable to use mixtures containing more than one or two HPV-DNAs for the diagnosis of each type of disease mentioned in the table as a consequence of its being recognized that other HPV-DNAs may be involved in the development of the same type of disease. The diagnosis

TABLE V

CHARACTERISTICS OF MIXTURES OF HPV-DNA UTILIZABLE FOR THE VIROLOGICAL DIAGNOSIS OF PAPILLOMAVIRUS INFECTIONS

| Designation of mixtures | Constitution[1] | Disease to be diagnosed |
|---|---|---|
| 1 | 1, 2d*, 4 | Cutaneous or mucosal warts (in particular, verrucae and plantar warts). |

TABLE V-continued

CHARACTERISTICS OF MIXTURES OF HPV-DNA UTILIZABLE FOR THE VIROLOGICAL DIAGNOSIS OF PAPILLOMAVIRUS INFECTIONS

| Designation of mixtures | Constitution[1] | Disease to be diagnosed |
|---|---|---|
|  |  | Differential diagnosis of epidermodysplasia verruciformis |
| 2 | 3, 10a, 10b*, 28*, 29* | Mucosal, cutaneous, intermediary or plane warts. Intra-epithelial neoplasias and cutaneous cancers. Differential diagnosis of epidermodysplasia verruciformis. |
| 3 | 5, 17a*, 24* | Epidermodysplasia verruciformis. Intra-epithelial neoplasias and cutaneous cancers. |
| 4 | 5, 8, 12, 14a*, 14b*, 19*, 20*, 21*, 22*, 23* | Epidermodysplasia verruciformis. |
| 5 | 9, 15*, 17a*, 17b* | Epidermodysplasia verruciformis. |
| 6 | 24* | Epidermodysplasia verruciformis. |
| 7 | 5, 8, 14b*, 32* | Cutaneous cancers of epidermodysplasia verruciformis. Intra-epithelial neoplasias and cutaneous cancers. |
| 8 | 13, 31* | Oral epithelial hyperplasia; differential diagnosis of oral intraepithelial neoplasias. |
| 9 | 32* | Intraepithelial neoplasias and cutaneous cancers. |

[1] The new HPV types introduced into the constitution of the mixtures of probes are indicated by an asterisk.

of the nature of the disease and its possible course will be the more efficacious, the higher the number of probes used. In addition, hybridization assays carried out with different mixtures of probes enable differential diagnoses to be made which, in turn, render more likely the correctness of the diagnosis of the disease from which the patient is suffering.

In Table V, only probes composed of HPV-DNAs isolated in the laboratory of the inventors have been mentioned. It will be obvious, in view of the preceding discussion, that the various mixtures can be advantageously supplemented with DNAs derived from HPVs isolated in other laboratories should these viruses have been found on different occasions in patients suffering from the same type of disease. For example, it can only be an advantage for mixture 7 to be supplemented with all of the other HPV-DNAs encountered in types of epidermodysplasia verruciformis which risk being transformed into intra-epithelial neoplasias and skin cancers. It will be noticed in Table V that some of the mixtures are presented as being characteristic for the diagnosis of identical diseases. Nonetheless, it is to be noted that different mixtures do distinguish between infections with a low risk of carcinogenesis and infections with a high risk of carcinogenesis. For example, hybridization occurring with a viral preparation derived from a patient subjected to diagnosis with mixture 7 provides evidence of a higher risk of skin carcinogenesis than the case in which hybridization occurs preferably with mixture 3.

Similarly, the EV detected by mixture 5 provides evidence of a higher risk of carcinogenesis than in EV detected by mixture 6. Mixture 4 detects EV presenting an even higher risk than those detected by mixture 5.

Other mixtures are cocktails of different HPV-DNAs (or probes containing these HPV-DNAs or fragments of the latter) will be described below which can be used in combination to carry out comprehensive diagnoses of different forms of papillomavirus infections, ultimately with the aim of providing a prognosis of the possible course the infection may take.

Preferred mixtures in accordance with the invention are indicated in Table V mentioned above.

The above table also indicates the nature of the diseases more likely to be diagnosed by the utilization of the mixtures presented at the left-hand side of the table. It will be recalled that the restriction maps of the other HPV-DNAs identified in the preceding table are presented in the FIGS. 1 to 9.

It is to be noted that HPV-IP2 may be considered as especially representative of probes which may be used for the detection of the risk of the development of genital neoplasias and, in particular, of cancers of the uterine cervix.

Thus, the invention relates more especially to diagnosis "kits" comprising at least ten groups appearing in the groups numbered 1 to 10 in the table under the heading "Designation of mixtures".

In the foregoing, particular consideration has been given to the use, as probes, of cloned, whole HPV-DNAs. The latter may however be replaced by cloned fragments of these DNAs, in particular, by the genes E1 or L1 and by the genes E6–E7.

The basic principle of in vitro detection of HPV-DNA naturally depends on hybridizations carried out under stringent or less stringent conditions. For example, one may proceed as follows, provided, of course, that it is understood that the diagnostic assays described are not to be considered as limiting with respect to the conditions under which probes or mixtures of probes according to the invention are used.

The aim of the investigations in which probes prepared from mixtures of cloned DNAs of HPVs are used is to demonstrate an HPV and to identify the type of HPV in a biopsy, in cells obtained by grattage of lesions, or in biopsy sections fixed with Carnoy mixture (ethanol, chloroform, acetic acid: 6:3:1) and embedded in paraffin. The investigation requires that the DNA be first extracted from samples according to known methods and involves the analysis of this DNA by molecular hybridization experiments, carried out under strict or less strict conditions using radioactive probes (labelled with $^{32}P$ or $^{35}S$) prepared from mixtures of HPV-DNAs. Each investigation usually requires that several mixtures of probes be used.

Several methods of hybridization may be used. For example, the method of dot blot hybridization may be employed. This method involves the denaturation of the DNA and the depositing of aliquots of the DNA on membranes (nitrocellulose or Genescreenplus), the hybridization of each membrane under standard conditions with a mixture of probes and the detection of the radioactive hybrids by exposure of the membrane to a radiographic film. The method of Southern hybridization may also be used. This method consists of the electrophoretic separation of the DNA fragments produced by treatment of the DNA with restriction enzymes in an agarose gel, the transfer of the fragments to membranes (nitrocellulose, Genescreenplus) after alkaline denaturation and their hybridization under standard conditions with different mixtures of probes. The formation of radioactive hybrids is detected after exposure of the membrane to radiographic film.

The radioactive probes are constituted either by the DNAs of HPVs labelled by the method of "nick-translation", or by RNAs prepared by transcribing the viral DNAs inserted into a vector of the SP6 type, for example. The use of radioactive probes offers the advantage of high sensitivity but that does not exclude the use of non-radioactive probes, biotinylated probes for example, capable of being recognized by antibodies either labelled themselves or recognized by antibodies bearing a marker such as an enzyme, fluorescence label, etc . . .

The choice of probes depends on the nature of the samples. Thus, for example, in the case of a patient suspected to be suffering from EV, the mixtures 1, 2, 3, 4, 5, 6 and 7 will be used. The mixtures 1 and 2 enable a differential diagnosis between EV and cutaneous warts to be made. Probe 3, containing the most frequently detected member of each of the three groups of HPVs associated with the disease, and the probe 7, containing the DNAs of the types of HPV associated with EV cancers, will permit the diagnosis of EV in the majority of cases and, in particular will lead to the identification of the patients infected with the types of HPV presenting risk of developing into cancers. The use of the mixtures 4, 5 and 6 makes it possible to define more precisely the type or types of HPV infecting this same patient.

Thus, the invention also relates to "kits" containing several probes of the type indicated above, in particular:

either representatives of each of the 19 types and subtypes of HPV-DNAs indicated above, or mixtures of probes, preferably the various groups or mixtures of probes which had been defined above, these "kits" being intended for in vitro diagnostic studies involving hybridization between the viral preparations obtained from patients and the various groups or mixtures.

It is obvious and also follows from the foregoing that the invention is in no way limited to those of its mode of application and realisation which have been given particular consideration; on the contrary, it includes all possible variants; in particular, the reference in the claims to a designation DNA-HPV, followed by a specific number corresponding to a DNA-HPV, the restriction map of which has been provided in the Figures, is to be understood as indicating that these claims cover all of the DNA-HPVs which have in common with this particular DNA-HPV properties allowing them to be classed as being of the same type, in accordance with the definition of the type given above and, with all the more reason, all of the DNA-HPVs which belong to the same subtype.

With particular regard to the DNA derived from HPV32, it is to be noted, and this is made clear in the diagrams, that this DNA is not cleaved by AvaI, BalI, BamHI, ClaI, EcoRI, HindIII, NdeI, NruI, PvuI, PvuII, SacI, SalI, SmaI, TthIII, XmaI.

It will be noted that the recombinant DNAs designated below were deposited with the C.N.C.M. (Collection Nationale des Cultures de Micro-Organismes de l'INSTITUT PASTEUR de Paris) on the 30th of Nov. 1984 under the numbers which appear below:

pBR322/HPV2d . . . No. I-379
pBR3222/HPV10bA . . . No. I-380
pBR322/HPV10bB . . . No. I-381
pBR32/HPV14a . . . No. I-382
pBR322/HPV14b . . . No. I-383
pBR322/HPV15 . . . No. I-384
pBR322/HPV17a . . . No. I-385
pHPV5 HindIIIB/HPV17b . . . No. I-386
pBR322/HPV19 . . . No. I-387
pBR322/HPV20 . . . No. I-388
pBR322/HPV21 . . . No. I-389
pHV5 HindIIIB/HPV22 . . . No. I-390
pBR322/HPV23 . . . No. I-391
pBR322/HPV24a . . . No. I-392
pBR322/HPV24b . . . No. I-393
pBR322/HPV28 . . . No. I-394
pBR322/HPV29 . . . No. I-395
pBR322/HPV31 . . . No. I-396
pSP64/HPV32 . . . No. I-397
pL155/IP2 . . . No. I-450
pSP65/IP4 . . . No. I-449

The invention also relates more particularly to the products expressed by the genes E6, E7 and especially L2 of the different papillomaviruses which have been mentioned in the discussion thus far.

These products of gene expression may themselves be used for the detection of papillomaviruses or products expressed by them in defined biological samples and for the identification of the papillomaviruses according to the types or subtypes to which they belong. The conditions under which these products of gene expression may be obtained will be illustrated in the remainder of this description, particularly with regard to the expression of the L2 sequence of papillomavirus HPV1a, it being understood that similar techniques may be used to induce the expression of the genetic sequences corresponding to L2 (or E6, E7 or L1) from other types of papillomavirus. In the discussion which follows, particular reference will be made to the sequences or genes corresponding to L2, it being nonetheless understood that the information furnished relating to the products of expression of the L2 genes may, if required, be applied to the products of expression of the other gene referred to above. Nonetheless, particular interest attaches to the products of expression of the L2 sequences, in that they may themselves be used for the in vivo production of antibodies capable of recognizing the products of expression of the L2 gene in biological samples infected with the corresponding papillomavirus but not with a papillomavirus of a different type, and more particularly when the preparations of this type have been fixed beforehand. The new procedure provided by the invention and which will be discussed later thus provides distinct agents which make it possible to determine the types of papillomavirus present in the lesion under study so that their severity can be assessed and the appropriate treatment chosen. The antibodies produced against the different types of products expressed by the L2 genes can be grouped in mixtures corresponding to those which were identified earlier in the context of the hybridization probes.

Consequently, the invention also provides "kits" containing several distinct antibodies which can be used in a series of tests to detect, and if necessary, identify or classify, the newly isolated papillomaviruses. For example, a kit in accordance with the invention contains a number of reagents constituted by distinct antibodies or mixtures of antibodies, for example reagents comprising antibodies formed against the products expressed by the L2 genes of papillomaviruses constituted in the following groups:

1) at least HPV2d,
2) at least one of the HPVs can be 10b, 28 and 29,
3) at least one of the HPVs 17 and 24, 4) at least one of the HPVs 14, 15, 17, 19, 20, 21, 22, 23 and IP4,
5) at least one of the HPVs 15 and 17,
6) HPV 24,
7) at least one of the HPVs 14, 32 and IP4,
8) HPV 31,
9) HPV 32,
10) at least one of the HPVs 16, 18 and IP2, it being understood that the antibodies of the ten groups are chosen in such a manner as to be different from each other under all circumstances should each of the ten groups be reduced to only one of the antibodies of which they are composed.

The antibodies formed against the products expressed by the L2 genes (or against recombinant proteins containing these products of expression fused with an additional polypeptide, in particular a stabilizing polypeptide which does not lead to the modification of the immunogenic properties of the product expressed by the L2 genes) are used for the direct detection of virus in histopathological sections derived from the lesions induced by the papillomaviruses in the subject infected by them. Advantageously, the detection is carried out on preparations fixed before-hand under dissociating conditions, for example, in the CARNOY mixture already cited (also described in the monograph by L. LISON, entitled "animal histochemistry and cytochemistry").

The anti-L2 antibodies, fixed if possible, may be recognized by other antibodies formed against the first antibodies and to these second antibodies appropriate markers, preferably non-radioactive ones, may be attached. For example, these markers may be enzymes or fluorescent probes.

Quite naturally, the invention also relates to the polypeptides themselves, which are the products of expression of the L2 genes of the papillomaviruses. These products of gene expression have already been referred to earlier as "L2 proteins". The invention also relates to the polypeptides in which this L2 protein is fused to other polypeptide sequences provided that these latter do not cause any critical modification of the immunogenic properties of the L2 protein. The presence of these other polypeptide fragments can arise notably from the method used to produce these hybrid polypeptides, particularly when they have been prepared by procedures involving the techniques of genetic engineering. Advantageously, the invention relates to hybrid polypeptides containing a sequence derived from beta-galactosidase. Such products may be obtained notably by transformation of E. coli with appropriate vectors (phages or plasmids ) modified by all or part of the lactose operon and containing, in addition, downstream of the lactose operon promoter (or any other appropriate promoter, for example of phage lambda) the nucleotide sequence derived from the L2 gene of a specific type of papillomavirus. It is an advantage to be able to make use of plasmids or phages of this type containing a part at least of the beta-galactosidase gene of the lactose operon.

The invention also relates to groups of distinct polypeptides, each group of polypeptides corresponding to only a part of the complete L2 proteins referred to above, it being nonetheless understood that these different groups of polypeptides each contains the antigenic sites characteristic of the L2 proteins of the type in question.

When they have been purified, the polypeptides according to the invention may also be employed in methods used to purify their corresponding antibodies, particularly from the sera of animals which have been immunized with these polypeptides. In particular, these polypeptides may be bound to affinity columns. The procedures for the purification of the antibodies then consist of allowing the serum containing them to pass through an affinity column to which the above-mentioned polypeptides are attached. The antibodies selectively bound to these columns can then be recovered by dissociation of the antibody-antigen complexes by means of an appropriate buffer of sufficient ionic strength, for example, a solution of a salt such as ammonium acetate. Acidic solutions may also be used.

Finally, the invention relates to mixtures involving these antigens (or groups of antigens) and antibodies (or groups of antibodies).

In particular, the invention relates to groups containing one or, preferably a "cocktail" of antibodies derived from sets of papillomaviruses, all of which are often reputed to be present in a given type of disease. These cocktails (containing these antibodies or groups of antibodies: mixtures of sera or preparation of purified antibodies in association with an appropriate pharmaceutical excipient) are then available for use by administration, in particular by the parenteral route, to the patient concerned for the treatment of a given disease, as soon as the latter has been diagnosed clinically. The diagnosis results from an in vitro diagnostic test performed on a cytological or histological sample taken from the patient or from an in vivo diagnostic test which has shown that the infectious papillomavirus belongs to a type similar to that of one of the set of papillomaviruses referred to above. These sera are then able to cause a regression of the infections induced by the corresponding types or sub-types of papillomaviruses.

Finally, the invention relates to the corresponding preparations of vaccines containing one or, preferably, several L2 proteins in combination with an acceptable pharmaceutical excipient adapted to the chosen route of administration, in particular to the parenteral route which is used in order to protect the patients from the high risk of being infected with the corresponding disease.

Finally, reference is made to articles, together with the appropriate literature references, which supplement the description of the state of the prior art to the extent that that may be necessary or prove useful for the reader's complete understanding of the text. In this sense, the content of these articles must thus be considered to constitute part of the description.

A preferred methodology for the production of an L2 protein (or a fragment of this protein) which makes use of a fragment of the L2 gene of a given papillomavirus in the proper reading frame will be illustrated in connection with the description of the construction of a vector incorporating such fragments in the proper reading frame, followed by a description of the conditions under which the expression of the L2 protein or the polypeptide fragment can be induced in E. coli. A procedure for the purification of the protein or the polypeptide as well as its use in the production of sera containing antibodies directed against the protein or polypeptide will also be described. It will be clear to the specialist that the L2 fragment used in the proper reading frame will need to be fused into the vector used each time in a manner such as to preserve the open reading frame. If possible, it is useful to carry out fusion with a gene coding for a protein which guarantees the stability or facilitates the subsequent purification of the hybrid protein thus formed.

Figure 11:
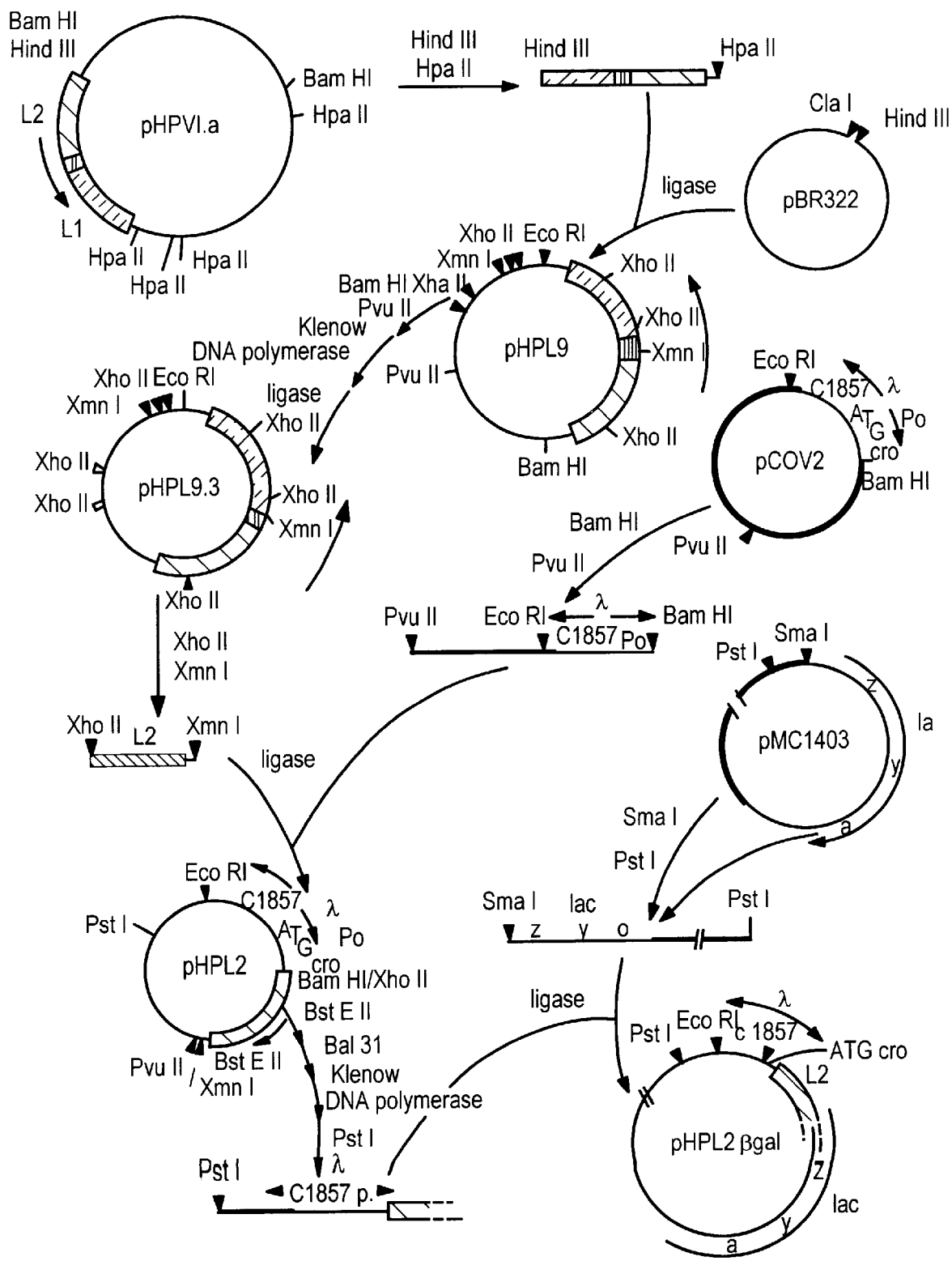
FIG. 11 is a diagrammatic representation of a method for the production of an L2 protein.

The steps of the production procedure are illustrated in FIG. 11 of the appendices.

MATERIALS AND METHODS
1) TREATMENT OF THE DNAS

For procedures relating to DNA recombination, the preparation of the plasmids and the DNA fragments, the formation of non-sticky ends, the digestion with the enzyme Bal 31 and finally the transfection of the cells, recourse was had to the methods of Maniatis, T. et al. (1982), described in the chapter entitled "Molecular cloning" in the monograph entitled "A Laboratory Manual", Cold Spring Harbor Laboratory, Cold Spring Harbor, N.Y., USA.

2) BACTERIA, PLASMIDS AND VIRUSES

The plasmid DNAs were obtained from pHPVI.a (Danos et al., 1982 and French patent 82 05887 of Apr. 5, 1982) contained in E. coli. (strain C600) pCQV2 expressed in the strain RRI (Queen, 1983) and pMC1403 expressed in strain MC1000 (Casadaban, 1983).

The intermediate plasmids constructed and the plasmid pHPL2 were passed several times in cultures of E. coli MM 294 and the plasmids pHPL2-beta-galactosidase in the strain MC1000 deficient in beta-galactosidase. The Lac+ strain were detected as red colonies on plaques of McConkey agar containing lactose (Silhavy et al., 1984, in "Experiments with gene fusions": Cold Spring Harbor Laboratory, Cold Spring Harbor, N.Y.).

The plasmids pHPL2 and pHPL2-beta-gal were then transfected into a lon⁻ strain deficient in protease, CAG1139 (Grossman et al., 1983, Cell 32, 151–159).

3) PREPARATION OF BACTERIAL LYSATES AND THEIR ANALYSIS ON POLYACRYLAMIDE GEL IN THE PRESENCE OF SODIUM DODECYLSULFATE (SDS-PAGE)

After being cultured overnight, CAG 1139 cells containing pHPL2 or pHPL2-beta-gal 116 were diluted 5 to 20 fold with LB medium. They were then grown at 30° C. until the optical density 600 had attained 0.5–0.9.

The PR-lambda promoter was then derepressed by growing the cells at 41° C. for 90 minutes. The cultures were then recentrifuged and the pellets collected and suspended in a medium of 62 mM Tris, pH 6.8, containing 2% SDS, 26% glycerol, 2 M 2-mercapto-ethanol and 0.03% bromophenol blue. A lysate of CAG 1139 cells not containing plasmid was used as control.

After being heated at 100° C. for 10 minutes, the samples were subjected to electrophoresis in a 10% SDS—polyacrylamide gel according to the technique of Laemmli (1970), Nature, 227, 680–684. BRL prestained proteins of known molecular weights were also subjected to electrophoresis.

The protein bands were visualized by treatment with a solution of he dye known as "Amido black" and transferred to a sheet of nitrocellulose or analysis by the method known as "Western Blot".

4) ANALYSIS

The analysis by "Western Blot" was carried out as described by Rosetto et al. (1984) J. Gen. Virol. 65, 1319–1324, by using papillomavirus polyclonal antibodies (Orth et al. (1978), Virology 91, 243–255 and Rosetto et al., already cited) and rabbit and guinea-pig anti-IgG immunoglobulins conjugated to horseradish peroxidase.

5) ANALYSIS OF ANTIBODIES

Use was made of the techniques of immunodiffusion, immunofluorescence and immunoperoxidase previously described (Orth et al., 1984, and Rosetto et al., 1984) in conjunction with purified HPV1.a viral particles or sections of the lesions induced by distinct types of papillomaviruses.

6) PURIFICATION OF L2-BETA-GALACTOSIDASE FUSION PROTEINS

A culture of CAG 1139 containing the plasmid pHPL2 beta-galactosidase 116 was diluted 200 fold with LB medium and the cells were then grown until they had attained O.D. 600 of 0.32. The culture was then brought rapidly to 41 ° C. and maintained at the higher temperature for 90 minutes.

The pellet of cells was resuspended in 20 mM Tris buffer, pH 7.5, containing 10 mM Mg $Cl_2$ and the cells were disrupted by sonication.

The fusion protein thus released into the medium was purified by affinity chromatography on a column of p-aminophenyl-B-D-thiogalactosidas (TPEG)-SEPHAROSE as described by Ullmann (1984). Gene 29, 27–31.

The fusion protein, purified as indicated above, was used to immunise female Harley guinea-pigs. The animals received three sub-cutaneous injections, at distinct sites, of about 150 micrograms of protein in the presence of complete Freund adjuvant (DIFCO) at intervals of two to three weeks. The serum was collected one week after the third injection.

RESULTS

CONSTRUCTION OF PLASMIDS CAPABLE OF EXPRESSING THE L2 OPEN READING FRAME IN *ESCHERICHIA COLI*

The constructs are presented in FIG. 11. The L2 open reading frame was cloned with a view to its expression in *Escherichia Coli* (*E. coli*). The pHPV1.a plasmid contains the entire genome of HPV1.a cloned at the BamHI site of the plasmid pBR322 by Danos et al. (EMBO J.1, p. 231–236, 1982). For the purpose of isolating open reading frames of the late region of the viral genome, a HpaII-HindIII fragment of a pHPV 1.a plasmid was subcloned into a pBR322 plasmid. The plasmid obtained was called pHPL9. This plasmid was shortened by removing a non-essential PVu II—BamHI fragment in the pBR322. From the resulting plasmid pHPL 9.3, a XmnI-XhoII fragment containing 1526 base pairs (b.p.) of the open reading frame minus the 318 base pairs of the 5' terminals was isolated.

The stop codon of the L2 open reading frame is conserved.

The L2 fragment obtained was then inserted into the expression vector pCQV2 (Queen 1983) in place of a non-essential PvuII-BamHI fragment. The L2 open reading frame is thus found directly adjacent to the ATG stop codon and to the SD sequence (Shine and Dalgarno, Proc. Natl. Acad. Sci. USA 71, p. 1342–1346, 1974) of the cro gene of the phage lambda and under the control of the PR lambda promoter. The promoter is regulated by the temperature-sensitive repressor CI857, which thus provides control of the production of the product expressed by the L2 gene. In this way, the plasmid pHPL2 was obtained in which the 1206 base pairs of the C terminal part of the L2 open reading frame are in phase with the ATG start codon of the cro gene of the lambda phage. The presence of a XhoII restriction site at the BamHI/Bgl II junction provided proof that the open reading frame had been maintained.

With the aim of stabilizing the L2 protein synthesized in *E. coli* and at the same time of making available a convenient method for its purification, it was also decided to allow it to be expressed as a hybrid protein fused with beta-galactosidase of *E. coli*.

In order to achieve this, the L2 terminal codon was eliminated after linearization of the pHPL2 plasmid at the BstEII site, followed by digestion with the enzyme Bal31.

This DNA, which contains the L2 gene and the sequences supplying the signals for transcription and translation, was shortened by digestion with PstI, before being inserted into the plasmid pMC1403 (Casadaban, Methods in Enzymology 100, p. 293–308, 1983) in place of the SmaI-PstI.

PMC1403 contains the lac operon without its promoter and the first 22 base pairs of the open reading frame for the gene of beta-galactosidase. The recombinant was transfected into MC 1000, lac⁻ cells. The production of beta-galactosidase in the clones obtained at high temperature provided a means to select on McConkey lactose agar plates (Silhavez et al., Cold Spring Harbor Laboratory, N.Y. 1984) the pHPL2—beta-gal plasmids in which the genes for L2 and beta-galactosidase are both in the open reading frame.

The pHPL2—beta-gal 116 clone, selected by such a procedure, was studied later.

The sequencing of the DNA (result not shown here) indicated that only the last two C terminal amino acids of the L2 open reading frame had been lost in the course of digestion with Bal 31 and that the product expressed by the L2 open reading frame was linked through a proline residue to the ninth amino acid of beta-galactosidase.

PRODUCTION OF PROTEINS RELATED TO HPV1.a BY CELLS TRANSFECTED WITH pHPL2 AND pHPL2—BETA-CAL 116

The plasmid pHPL2 has the capacity to code for an L2 protein of about 51.2 Kd and the pHPL2-beta-gal plasmid for a hybrid protein of about 167 Kd.

In order to study the production of proteins by these plasmids, the latter were first transfected into a strain of *E. coli* CAG 1139 1on⁻, which is protease deficient. The cells were then cultivated at 30° C. before being brought to 41° C. in order to induce the production of the proteins under the control of the PR lambda promoter. The bacterial lysates obtained were electrophoresed on an SDS—polyacrylamide gel.

The proteins related to this virus HPV1.a were detected by analysis by means of the technique called "Western Blot" using anti-HPV1.a virus antibodies. For the cells grown at 30° C., the analytical results were the same, whether or not they contained a plasmid. However, in the case of the cells induced at 41° C., specific bands of protein were demonstrated in the transfected cells: among the proteins isolated from the cells transfected with the recombinant pHPL2-beta-gal 116, it was possible to isolate a main band having the expected molecular weight of approximately 167 Kd, corresponding to an L2 beta-galactosidase (L2-beta-gal) fusion protein, and several minor bands of molecular weights of about 58 Kd, probably resulting from proteolytic degradation.

The plasmid. pHPL2 gave rise to a protein band of about 72 Kd. This molecular weight is higher than the expected one of 51.2 Kd. The significance of this difference remains to be elucidated.

In order, then, to be able to study the antigenicity of the protein produced in *E. coli*, the L2-beta-gal product was purified from the bacteria lysate of a culture induced by heat, by means of affinity chromatography on a column of TPEG-SEPHAROSE (Ullman, Gene 29, p. 27–31, 1984). The proteins eluted from the column were analysed from an SDS-polyacrylamide gel. Staining with "Amido-Black" revealed three principle protein bands, one with a high molecular weight probably corresponding to the hybrid protein L2-beta-gal, the second migrating together with purified beta-galactosidase and a third with a molecular weight of about 60 Kd.

This protein with the low molecular weight may be a contaminant. Analysis by the technique of "Western Blot" with a specific antibody of the HPV1.a type reveals a main band of high molecular weight corresponding to the product expressed by the fused L2-beta-gal gene and several minor bands (FIG. 3b).

Immunogenicity of the L2-beta-gal product

In order to test the immunogenicity of the fusion protein, the product eluted was injected into two guinea-pigs. The sera were collected after the third injection. By means of a "Western Blot" analysis, the sera obtained reacted with bands migrating as the L2-beta-gal fusion protein or as the L2 product in the bacterial lysates derived from cultures containing the plasmids pHPL2-beta-gal 116 and pHPL2, respectively, and which had been induced by a temperature shift.

In the two types of cell lysate the sera recognized proteins (about 60 and 55 Kd) which were also found in the control lysate CAG 1139. At least one of these proteins appeared to correspond to the protein copurified with the L2-beta-gal fusion protein and beta-galactosidase.

The sera recognized proteins of about 80 Kd in a dissociated HPV1.a viral preparation (treated with a detergent) and in an extract of a wart induced by HPV1.a.

In an immunodiffusion test, the guinea-pig sera obtained did not precipitate the intact HPV1a virus particles used as antigen, a finding which indicates once again that the viral antigens recognized by the serum in the immune transfer technique are not available at the surface of the virion or that they are not precipitated by the sera.

The sera induced by the products expressed by the L2 gene did not react with frozen sections of HPV1a warts which are known to preserve the native conformational structure of the virions and of the viral polypeptides. This result testifies once again to the fact that the antibodies are not directed against a conformational antigen.

The sera reacted only slightly (at a dilution of 1/50) with sections of warts infected with HPV1a which had been fixed in BOUIN medium. This result confirms the specific character of the type of antigens involved as opposed to groups of antigens which should lead to stronger antibody-antigen reactions with sections infected by a virus and fixed in BOUIN medium.

On the other hand, the observations made on sections fixed in CARNOY medium presented evidence of positive reactions both with the type antigens and the group antigens. In particular, it was observed that the guinea-pig sera gave very strong antibody-antigen reactions (even at a dilution of 1/1000) when the section contained a virus of the same type as that which had furnished the antigen which had served to induce the antibodies used in the assay. On the other hand, no immunological cross-reaction was observed when the serum under study was placed in contact with sections containing a virus belonging to a different type.

It needs also to be pointed out that the type antigens considered are not necessarily always the same as the types such as those defined above with regard to the mutual capacities for hybridization of genomes of two distinct papillomaviruses.

In particular, it is important to bear in mind the distinction between two kinds of antigens in papillomaviruses:

the type antigens, characterized by the absence of an antigenic cross-reaction between the different kinds of papillomavirus when using antibodies obtained by injection of whole virions, and the group antigens essentially masked in the virion, and the presence of which is demonstrated by antibodies after injection of dissociated viral particles.

The papillomaviruses belonging to different types in the assays of antigen-antibody reactions are those for which the L2 coding sequences, from which their respective homologous regions have preferably been removed, code for polypeptides which do not give rise to antibody-antigen cross-reactions with their respective antibodies.

Preferred types of antigens are those which are coded by the open reading frames of the L2 gene lacking the N terminal region, comprising in particular up to ¼ of the length of the L2 regions in question.

Finally, the invention also relates to a test for the detection of those polypeptides coded by the L2 regions which do not give cross-reactions, in viruses belonging to different types. These polypeptides may be defined as those, the antibodies of which react efficaciously with viruses contained in cytological or histological sections fixed in Carnoy medium, but which react poorly, if at all, with the same sections when these latter are fixed in Bouin medium.

The invention also relates to a procedure for the classification of new papillomaviruses relative to known papillomaviruses. The procedure is characterized in that, after hybridization of its genome under non-stringent conditions with the L2 region of one or several genomes of known papillomaviruses or, if the occasion arises, sequencing of its genome, and the consequent identification of the open-reading frame for the L2 gene, a recombinant is produced between a fragment consisting of all or part of this L2 gene which has been excised from the said genome beforehand and an appropriate vector. Then the expression of the fragment is induced in host cell or appropriate microorganisms, in particular *E. coli*; if desired, antibodies are produced in vivo against the products of expression which have been obtained and assays of antibody-antigen cross-reactions are carried out between either the products expressed by the L2 genes of the newly isolated papillomavirus or the corresponding antibodies, on the one hand, and either the antibodies or the antigens corresponding to papillomaviruses of known types, on the other. The type of the newly isolated papillomavirus can then be distinguished from or identified with those of known papillomaviruses, depending on whether the antigen-antibody cross-reactions give negative or positive results.

Finally, the invention also relates to the diagnostic procedure which includes the identification of the type of infectious virus which may be present in a patient and consists of allowing antigens previously obtained from viruses belonging to different types to react with a biological sample, in particular a serum sample, taken from the patient on whom the test is being conducted.

The infectious virus will be assumed to belong to a specific type when an antibody-antigen reaction is observed between a serum sample and an antigen derived from a papillomavirus belonging to the same type. These diagnostic assays may be carried out, for example, by using the ELISA method.

More particularly, the invention relates to a procedure for the identification of an infectious papillomavirus in a sample taken from a patient such as tissue or fluid, for example serum, with a given type of papillomavirus. This procedure is characterized by placing this biological sample in contact with antibodies which had previously been formed against the product expressed by a DNA containing at least a part of the L2 region of the genome of a virus belonging to this type, this admixing being performed under conditions and for a time which allowed an immunological reaction to take place. The detection of the formation of an antibody-antigen complex then provides evidence for the presence of a papillomavirus of a type identical or related to that which had given rise to the test antibodies.

Preferably, the DNA containing the L2 region or a part of it was cloned in a competent host cell such as a bacterium, for example, *E. coli*.

Advantageously, the part of the L2 region utilized corresponds to the open reading frame for the L2 gene lacking the N-terminal region, which is not characteristic of the type. Preferably, this N-terminal region corresponds to the first quarter of the reading frame.

More particularly, the invention relates to a detection procedure of this type in which the DNA containing the above-mentioned part of the L2 region (or the entire L2 region) is a DNA hybrid formed from a nucleic acid coding for a protein normally expressed in the chosen competent host cell and in which the above-mentioned L2 region has been incorporated beforehand, in particular by in vitro recombination.

For example, the protein normally expressed in the host cell corresponds to all or part of beta-galactosidase, when the host cell is *E. coli*.

The detection procedure according to the invention is applicable to all histological sections which have been fixed, preferably in Carnoy mixture, and also directly to a serum sample.

The procedure according to the invention also comprises the addition of the biological sample under the above-mentioned conditions to "cocktails" of antibodies previously formed against products expressed by the L2 genes—or part of them—derived from several viruses of the same types or of related types, in particular of viruses classified in the same manner as that indicated above with respect to the DNA probes.

The use of these "cocktails" of antibodies under conditions similar to those which were mentioned in connection with the DNA probes thus enable correlations to be made between the group to which a given papillomavirus belong and the disease from which the patient under study is suffering or to which he is potentially exposed.

Finally, the invention relates to a procedure for the preparation of each of the above mentioned hybrid polypeptides and antibodies corresponding to them.

This procedure comprises:

the incorporation, in vitro in particular, of the whole or part of the L2 region of the genome of the papillomavirus concerned into an appropriate vector;

the transformation of a competent host cell with the vector thus modified, i.e. a host capable of expressing the whole or part of the above-mentioned L2 region;

the recovery and, preferably, the separation of the polypeptide resulting from the expression of the whole or part of the L2 region, this polypeptide being capable of inducing in vivo the production of antibodies capable of detecting papillomavirus proteins under the condition set out above.

The invention also concerns the procedure for the production of the said antibodies, characterized by the immunization of an animal, a rabbit for example, with the above-mentioned polypeptides, and the recovery of the antibodies formed.

Finally, the invention may be extended to include the classification of either the hybrid peptides or the antibodies, obtained from various papillomaviruses according to the different types to which they prove to belong.

REFERENCES (1) Derst, M. et al., 1983, Proc. Natl. Acad. Sci. U.S.A., 80, 3812–3815.

(2) Coggin, J. R., Jr. et al., 1979, Cancer Res., 39, 545–546.

(3) Gissmann, L. et al., 1982, J. Virol. 44, 393–400.

(4) Green, M. et al., 1982, Proc. Natl. Acad. Sci. U.S.A. 79, 4437–4441.

(5) Heilman, C. A. et al., 1980, Virol. 36, 395–407.

(6) Jablonska, S. et al., 1972, Cancer Res., 32, 583–589.

(7) Jablonska, S. et al., 1982, Springer Semin. Immunopathol. 5, 33–62.

(8) Kremsdorf, D. et al., 1982, J. Virol. 43, 436–447.

(9) Kremsdorf, D. et al., 1983, J. Virol. 48, 340–351.

(10) Lutzner, M. A. et al., 1978, Bull. Cancer, 65, 169–182.

(11) Lutzner, M. A. et al., 1983, Lancet ii, 422–424.

(12) Migozzi, M. et al., 1965, Bull. Soc. Franc. Derm. Syph. 72, 747–748.

(13) Orth, G. et al., 1980, Cold Spring Harbor Conf. Cell Proliferation, 7, 259–282.

(14) Orth, G. et al., 1981, J. Invest. Dermatol. 76, 97–102.

(15) Orth, G. et al., 1979, Cancer Res. 39, 1074–1082.

(16) Ostrow, R. S. et al., 1982, Proc. Natl. Acad. Sci. U.S.A. 79, 1634–1638.

(17) Ostrow, R. S. et al., 1983, Ann. Acad. Dermatol. 8, 398–404.

(18) Pfister, H. et al., 1983, Cancer Res. 43, 1436–1441.

(19) Pfister, H. et al., 1983, J. Virol. 47, 363–366.

(20) Pfister, H. et al., 1981, Int. J. Cancer, 27, 645–650.

(21) Rueda, L. A. et al., 1976, Med. Cut. I.L.A. 2, 113–136.

(22) Ruiter, M. et al. J Invest. Dermatol., 47, 247–252.

(23) Sutcliffe, J. G., 1978, Nucleic Acids Res. 5, 2721–2728.

(24) Tsumori, T. et al., 1983, J. Gen. Virol. 64, 967–969.

We claim:

1. An isolated antibody that specifically binds to a papillomavirus L2 protein, wherein said antibody:

binds a papillomavirus L2 protein which lacks the N-terminal homologous region comprised in the N-terminal 25% of the amino acid residues of the entire papillomavirus L2 protein, and, does not cross react with L2 proteins encoded by DNA sequences of papillomaviruses which exhibit cross-hybridization of less than 50% with said papillomavirus DNA sequences under stringent conditions, and wherein said papillomavirus is selected from HPV 1a, HPV 2d, HPV 10a, HPV 10b, HPV 14a, HPV 14b, HPV 15, HPV 17a, HPV 17b, HPV 19, HPV 20, HPV 21, HPV 22, HPV 23, HPV 24, HPV 28, HPV 29, HPV 31, HPV 32, HPV IP2 and HPV IP4.

2. The antibody according to claim 1, wherein said papillomavirus is papillomavirus HPV 1a.

3. A method of in vitro detection of the presence of papillomavirus infection, said method comprising:

(i) obtaining a sample from a patient suspected of papillomavirus infection, (ii) contacting said sample with the antibody according to claim 1, and iii) detecting the presence of antibodies bound to said sample as an indication of the presence of papillomavirus infection.

4. A composition comprising the antibody or a mixture of antibodies according to claim 1.

5. A method of in vitro detection of the presence of papillomavirus infection, said method comprising:

(i) obtaining a sample from a patient suspected of papillomavirus infection, (ii) contacting said sample with the composition according to claim 4, and iii) detecting the presence of antibodies bound to said sample as an indication of the presence of papillomavirus infection.

6. A composition comprising an isolated antibody that binds an HPV1a L2 protein which lacks the N-terminal homologous region comprised in the N-terminal 25% of the amino acid residues of the entire papillomavirus L2 protein and that does not specifically bind L2 proteins encoded by DNA sequences of papillomaviruses which exhibit cross-hybridization of less than 50% with said PHV1a papillomavirus DNA sequences under stringent conditions.

* * * * *

UNITED STATES PATENT AND TRADEMARK OFFICE
CERTIFICATE OF CORRECTION

PATENT NO. : 5,955,260
DATED : September 21, 1999
INVENTOR(S) : Komly et al.

It is certified that error appears in the above-identified patent and that said Letters Patent is hereby corrected as shown below:

Column 28,
Line 38, "PHV1a" should be -- HPV1a --.

Signed and Sealed this

Ninth Day of August, 2005

JON W. DUDAS
*Director of the United States Patent and Trademark Office*